United States Patent
Williams et al.

(10) Patent No.: US 6,350,593 B1
(45) Date of Patent: Feb. 26, 2002

(54) RECEPTORS FOR FIBROBLAST GROWTH FACTORS

(75) Inventors: Lewis T. Williams; Daniel F. Johnson, both of San Francisco; Pauline E Lee, San Diego, all of CA (US)

(73) Assignee: Regents of the University of California, Alameda, CA (US)

( * ) Notice: Subject to any disclaimer, the term of this patent is extended or adjusted under 35 U.S.C. 154(b) by 0 days.

(21) Appl. No.: 08/459,395

(22) Filed: Jun. 2, 1995

Related U.S. Application Data

(60) Division of application No. 07/834,311, filed on Feb. 13, 1992, which is a continuation-in-part of application No. 07/377,003, filed on Jul. 6, 1989, now abandoned.

(51) Int. Cl.$^7$ ............................................. C12N 15/09
(52) U.S. Cl. ...................... 435/69.4; 435/69.1; 435/325; 435/252.3; 435/240.2; 435/320.1; 536/23.5; 536/24.31; 530/350
(58) Field of Search ............................ 536/23.5, 24.31; 435/69.1, 69.4, 252.3, 320.1, 240.2, 325; 530/350

(56) References Cited

U.S. PATENT DOCUMENTS

| | | | |
|---|---|---|---|
| 4,394,443 A | 7/1983 | Weissman et al. ............. 435/6 |
| 4,668,476 A | 5/1987 | Bridgham et al. ............ 422/62 |
| 4,761,371 A | 8/1988 | Bell et al. .................... 435/69.1 |
| 4,785,079 A | 11/1988 | Gospodarowicz et al. .. 530/399 |
| 4,859,609 A | 8/1989 | Dull et al. ................... 436/501 |
| 4,968,607 A | 11/1990 | Dower et al. ................ 530/351 |
| 5,081,228 A | * 1/1992 | Dower et al. ................ 530/351 |
| 5,225,538 A | * 7/1993 | Capon et al. ............. 530/387.3 |
| 5,229,501 A | 7/1993 | Keifer et al. ................ 530/399 |

FOREIGN PATENT DOCUMENTS

| | | |
|---|---|---|
| WO | WO 90/05522 | 5/1990 |
| WO | WO 91/00916 | 1/1991 |

OTHER PUBLICATIONS

Herrera et al. J. Biol. Chem. 261, 2489–2491, 1986.*
Meinkoth et al. in Guide to Molecular Cloning Technique, Berger and Kummell eds. Methods in Enzymology, vol. 152, p. 91, 1987.*
Lee et al., *Clinical Research*, vol. 37, No. 2, p. 519A, (1989).
Baird, et al., *Proc. Nat'l. Acad. Sci. USA*, vol. 85, pp. 2324–2328, 1988.
Burrus, et al., *J. of Biol. Chem.*, vol. 264, pp. 18647–18653, 1989.
Clark–Lewis, et al., *Science*, vol. 231, pp. 134–139, 1986.
Feige, et al., *J. of Biol. Chem.*, vol. 263 No. 28, pp. 14023–14029, 1988.
Gospodarowicz, et al., *Endocrine Rev.*, vol. 8, pp. 95–114., 1987.
Hunkapiller, et al., *Meth. Enzymol.*, vol. 91, pp. 399–413, 1983.
Imamura, et al., *Biochem. Biophys. Res. Commun.*, vol. 155, pp. 583–590, 1988.
Isacchi, et al., *Nuc. Acids Res.*, vol. 18, p. 2616, 1990.
Itoh, et al., *Biochem. Biophys. Res. Commun.*, vol. 169, pp. 680–685, 1990.
Klein, *Immunology: The Science of Self–Nonself Discrimination*, John Wiley & Sons, New York, pp. 251–252 & 551–555, 1982.
Kornbluth, et al., *Mol. Cell. Biol.*, vol. 8, pp. 5541–5544, 1988.
Lee, et al., *Science*, vol. 245, pp. 57–245, 1989.
Lee, et al., *Nat'l. Mtg.—Am. Soc. Clin. Invest.*, vol. 37, p. 519A, 1989.
Lee, et al., *J. Cell. Biochem.—Suppl. 13B*, vol. 155, abstract #E513, 1989.
Mascarelli, et al., *Biochem. Biophys. Res. Commun.*, vol. 146, pp. 478–486, 1987.
Neufeld, et al., *J. Biol. Chem.*, vol. 261, pp. 5631–5637, 1986.
Neufeld, et al., *J. Cell. Physiol.*, vol. 136, pp. 537–542, 1988.
Olwin, et al., *J. Cell. Biol.*, vol. 103, p. 2979, 1986.
Pasquale, et al., *Proc. Nat'l. Acad. Sci. USA*, vol. 86 No. 14, pp. 5449–5453, 1989.
Pasquale, et al., Accession No. M24637. This nucleotide sequence was available through Gene Bank on or about Jun. 15, 1989.
Reid, et al., *Proc. Nat'l. Acad. Sci. USA*, vol. 87, pp. 1596–1600, 1990.
Risau, et al., *EMBO J.*, vol. 7, pp. 959–962, 1988.
Ruta, et al., *Oncogene*, vol. 3, pp. 9–14, 1988.
Ruta, et al., *Proc. Nat'l. Acad. Sci. USA*, vol. 86, pp. 8722–8726, 1989.
Safran, et al., *Oncogene*, vol. 5, pp. 635–643, 1990.
Yarden, et al., *Nature*, vol. 323, pp. 226–232, 1986.

* cited by examiner

*Primary Examiner*—Lorraine Spector
*Assistant Examiner*—Eileen B. O'Hara
(74) *Attorney, Agent, or Firm*—Townsend and Townsend and Crew LLP

(57) ABSTRACT

A fibroblast growth factor (FGF) receptor including a basic fibroblast growth factor receptor has been purified. Various forms have bee identified including soluble forms lacking any transmembrane segment. DNA sequences encoding full-length fibroblast growth factor receptors and polypeptides comprising a portion of an FGF-R ligand-binding domain have been isolated and sequenced. These DNAs include DNAs encoding for a basic FGF-R and a human FGF-R and are operably linked to control sequences and expressed in a culture of a compatible host transformed, transfected or electroporated by a cloning vehicle containing the DNA sequence. The invention also comprises antibodies to the receptor, methods of synthesizing the growth factor receptor proteins, methods for providing analogs of the fibroblast growth factor receptors. Methods for evaluating compositions which promoter or inhibit fibroblastic growth factors and compositions which are agonistic or antagonistic to fibroblast growth factor receptors are also provided. Diagnostic and therapeutic uses are described.

26 Claims, 17 Drawing Sheets

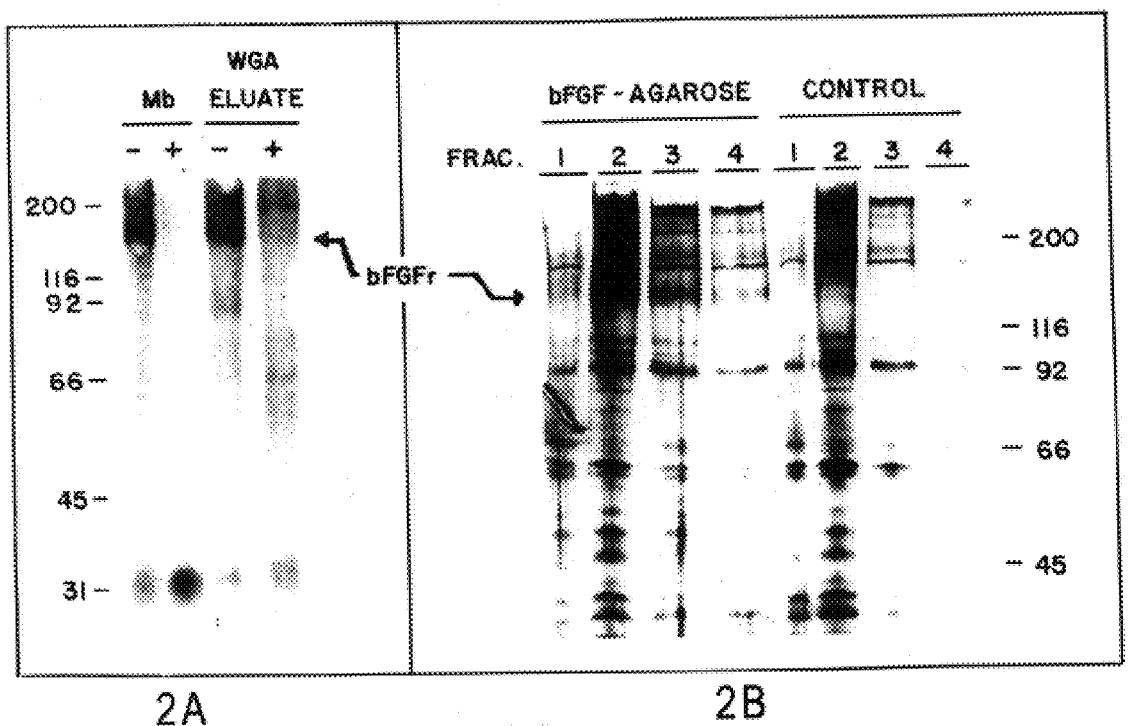
FIG._2.

```
  1 GGGGACCGGGCGGTGCGGGCAGCGCTGAGCGGCGGCCGTCGGGGCGGACCGCGCCTCCC
    GGGAGCGCCTCCCGGCCGCCACCTCGGGGCGGGGTCCGCCATGGGGCGGCCGCAGTGAGC
120 GCGGCGGCGGCGGGGCTGCGCTCTCGCCCCGGCCGGGGGTCCCCTCCATTGTTCCCGGG
    AGCGGCGGGCACCGCGCCTCCGCCGCGCCCGCGGGACTCCGCTCACAGCGGCCGACGGG
                                                              1
                                                              Met
239 GCCCCATGGAGGGGCGGTTGAGCGCAGTCGCTGAGCAGTAGCCGCAGCAGTGGG ATG
                                   10
    Phe Thr Trp Arg Cys Leu Ile Leu Trp Ala Val Leu Val Thr Ala
    TTT ACC TGG AGG TGC CTC ATC CTT TGG GCT GTG CTG GTC ACA GCC
                  20                              30
    Thr Leu Ser Ala Ala Arg Pro Ala Pro Thr Leu Pro Asp Gln Ala
341 ACG CTG TCT GCT GCC AGA CCG GCC CCC ACG CTG CCC GAC CAA GCT
                                   40
    Leu Pro Lys Ala Asn Ile Glu Val Glu Ser His Ser Ala His Pro
    CTG CCC AAA GCG AAC ATC GAG GTG GAG TCC CAC TCG GCG CAC CCC
              50                                       60
    Gly Asp Leu Leu Gln Leu Arg Cys Arg Leu Arg Asp Asp Val Gln
431 GGC GAT CTC CTC CAG CTG CGC TGC CGG CTG CGG GAT GAC GTG CAG
                                   70
    Ser Ile Asn Trp Val Arg Asp Gly Val Gln Leu Pro Glu Asn Asn
    AGC ATC AAC TGG GTG CGT GAT GGA GTG CAG CTG CCC GAG AAC AAC
                  80                              90
    Arg Thr Arg Ile Thr Gly Glu Glu Val Glu Val Arg Asp Arg Val
521 CGC ACG CGC ATC ACC GGC GAG GAG GTA GAG GTG CGG GAC CGG GTG
                                   100
    Pro Glu Asp Ser Gly Leu Tyr Ala Cys Met Thr Asn Ser Pro Ser
    CCC GAG GAC TCG GGG CTC TAT GCC TGC ATG ACC AAC AGC CCC TCG
              110                                      120
    Gly Ser Glu Thr Thr Tyr Phe Ser Val Asn Val Ser Asp Ala Leu
611 GGG AGC GAG ACC ACC TAC TTC TCC GTC AAC GTC TCA GAC GCA CTC
                                   130
    Pro Ser Ala Glu Asp Asp Asp Asp Glu Asp Asp Ser Ser Ser Glu
    CCT TCT GCA GAG GAT GAT GAT GAT GAA GAT GAT TCC TCC TCG GAG
              140                                      150
    Glu Lys Glu Ala Asp Asn Thr Lys Pro Asn Gln Ala Val Ala Pro
701 GAG AAG GAG GCG GAT AAC ACC AAG CCG AAC CAG GCT GTA GCT CCT
                                   160
    Tyr Trp Thr Tyr Pro Glu Lys Met Glu Lys Lys Leu His Ala Val
    TAC TGG ACC TAT CCC GAG AAG ATG GAG AAG AAG CTG CAT GCC GTC
              170                                      180
    Pro Ala Ala Lys Thr Val Lys Phe Lys Cys Pro Ser Gly Gly Thr
791 CCC GCT GCC AAA ACA GTG AAG TTC AAG TGC CCC TCA GGT GGG ACG
                                   190
    Pro Asn Pro Thr Leu Arg Trp Leu Lys Asn Gly Lys Glu Phe Lys
    CCC AAC CCC ACG CTG CGC TGG CTG AAG AAC GGC AAG GAG TTC AAG
```

FIG. 3A

```
            Pro Asp His Arg Ile Gly Gly Tyr Lys Val Arg Tyr Ala Thr Trp
                        200                                   210
 881    CCT GAC CAC CGC ATC GGG GGG TAC AAG GTC CGC TAT GCC ACC TGG

Ser Ile Ile Met Asp Ser Val Val Pro Ser Asp Lys Gly Asn Tyr
                                        220
        AGC ATC ATC ATG GAC TCG GTG GTG CCA TCA GAT AAG GGC AAC TAC

Thr Cys Ile Val Glu Asn Lys Tyr Gly Ser Ile Asn His Thr Tyr
                230                                   240
 971    ACG TGC ATC GTG GAG AAC AAA TAC GGG AGC ATC AAC CAC ACC TAC

Gln Leu Asp Val Val Glu Arg Ser Pro His Arg Pro Ile Leu Gln
                                        250
        CAG CTG GAT GTC GTG GAG CGC TCC CCG CAT CGG CCC ATC CTG CAG

Ala Gly Leu Pro Ala Asn Lys Thr Val Ala Leu Gly Ser Asn Val
                260                                   270
1061    GCA GGG CTC CCC GCC AAC AAA ACG GTG GCC CTG GGC AGC AAC GTG

Glu Phe Val Cys Lys Val Tyr Ser Asp Pro Gln Pro His Ile Gln
                                280
        GAG TTT GTC TGC AAG GTC TAC AGC GAC CCG CAG CCC CAC ATC CAG

Trp Leu Lys His Ile Glu Val Asn Gly Ser Lys Ile Gly Pro Asp
                        290                                   300
1151    TGG CTG AAA CAC ATC GAG GTG AAC GGC AGC AAG ATC GGC CCC GAC

Asn Leu Pro Tyr Val Gln Ile Leu Lys Thr Ala Gly Val Asn Thr
                                        310
        AAC TTG CCC TAC GTG CAG ATC CTG AAG ACG GCT GGC GTT AAC ACG

Thr Asp Lys Glu Met Glu Val Leu His Leu Arg Asn Val Ser Phe
                        320                                   330
1241    ACA GAC AAA GAG ATG GAA GTC CTT CAC TTA AGG AAT GTC TCA TTT

Glu Asp Ala Gly Glu Tyr Thr Cys Leu Ala Gly Asn Ser Ile Gly
                                        340
        GAG GAT GCT GGG GAG TAT ACA TGT TTG GCG GGT AAT TCT ATT GGG

Ile Ser His His Ser Ala Trp Leu Thr Val Leu Glu Ala Thr Glu
                    350                                   360
1331    ATC TCC CAT CAC TCT GCA TGG TTG ACA GTT CTC GAA GCT ACT GAG

Gln Ser Pro Ala Met Met Thr Ser Pro Leu Tyr Leu Glu Ile Ile
                                        370
        CAG TCA CCA GCC ATG ATG ACG TCC CGC CTC TAC CTG GAG ATC ATC

Ile Tyr Cys Thr Gly Ala Phe Leu Ile Ser Cys Met Val Val Thr
                    380                                       390
1421    ATT TAC TGC ACC GGC GCC TTC CTC ATC TCC TGC ATG GTG GTG ACA

Val Ile Ile Tyr Lys Met Lys Ser Thr Thr Lys Lys Thr Asp Phe
                                    400
        GTC ATC ATC TAC AAG ATG AAG AGC ACC ACC AAG AAG ACA GAC TTC
```

FIG. 3B

```
              410                                               420
      Asn Ser Gln Leu Ala Val His Lys Leu Ala Lys Ser Ile Pro Leu
1511  AAC AGC CAG CTG GCC GTG CAC AAG CTG GCC AAG AGC ATC CCA CTG

430
      Arg Arg Gln Val Thr Val Ser Ala Asp Ser Ser Ser Ser Met Asn
      CGC AGA CAG GTA ACA GTG TCA GCA GAT TCC AGC TCC TCC ATG AAC 440                                     450
      Ser Gly Val Met Leu Val Arg Pro Ser Arg Leu Ser Ser Ser Gly
1601  TCG GGT GTG ATG TTG GTG CGG CCC TCA CGG CTC TCC TCC AGC GGA

460
      Thr Pro Met Leu Ala Gly Val Ser Glu Tyr Glu Leu Pro Glu Asp
      ACC CCC ATG CTG GCC GGC GTC TCC GAG TAT GAG CTG CCC GAG GAC
                    470                                 480
      Pro Arg Trp Glu Leu Pro Arg Asp Arg Leu Ile Leu Gly Lys Pro
1691  CCG CGC TGG GAG CTG CCA CGG GAC AGG CTG ATC CTG GGC AAG CCG

490
      Leu Gly Glu Gly Cys Phe Gly Gln Val Val Leu Ala Glu Ala Ile
      CTG GGA GAA GGC TGC TTT GGG CAG GTG GTG CTC GCG GAG GCC ATC 500                                    510
      Gly Leu Asp Lys Asp Lys Pro Asn Arg Val Thr Lys Val Ala Val
1781  GGC CTG GAC AAG GAC AAG CCA AAC CGC GTC ACC AAA GTG GCT GTA

520
      Lys Met Leu Lys Ser Asp Ala Thr Glu Lys Asp Leu Ser Asp Leu
      AAG ATG CTC AAG TCC GAT GCC ACA GAG AAG GAC CTG TCC GAC CTC 530                                         540
      Ile Ser Glu Met Glu Met Met Lys Met Ile Gly Lys His Lys Asn
1871  ATC TCC GAG ATG GAG ATG ATG AAG ATG ATC GGC AAG CAC AAG AAC

550
      Ile Ile Asn Leu Leu Gly Ala Cys Thr Gln Asp Gly Pro Leu Tyr
      ATC ATC AAC CTG CTG GGT GCC TGC ACG CAG GAC GGG CCC CTC TAT 560                                     570
      Val Ile Val Glu Tyr Ala Ser Lys Gly Asn Leu Arg Glu Tyr Leu
1961  GTC ATC GTG GAG TAC GCC AGC AAA GGC AAC CTG CGT GAG TAC CTG

580
      Gln Ala Arg Arg Pro Pro Gly Met Glu Tyr Cys Tyr Asn Pro Thr
      CAG GCA CGG CGC CCA CCG GGC ATG GAG TAC TGC TAC AAC CCC ACA 590                                         600
      Arg Ile Pro Glu Glu Gln Leu Ser Phe Lys Asp Leu Val Ser Cys
2051  CGC ATC CCC GAG GAG CAG CTC TCC TTC AAG GAC CTG GTG TCC TGC

610
      Ala Tyr Gln Val Ala Arg Gly Met Glu Tyr Leu Ala Ser Lys Lys
      GCG TAC CAG GTG GCA CGC GGC ATG GAG TAC CTG GCC TCC AAA AAG 620                                           630
      Cys Ile His Arg Asp Leu Ala Ala Arg Asn Val Leu Val Thr Glu
2141  TGC ATC CAC AGG GAC CTG GCG GCC AGG AAC GTG CTG GTG ACC GAG
```

FIG. 3C

```
         Asp Asn Val Met Lys Ile Ala Asp Phe Gly Leu Ala Arg Asp Ile
                                          640
         GAC AAC GTG ATG AAG ATC GCT GAC TTC GGG CTG GCC CGC GAC ATC
                         650                                    660
         His His Ile Asn Tyr Tyr Lys Lys Thr Thr Asn Gly Arg Leu Pro
    2231 CAC CAC ATC GAT TAC TAC AAG AAG ACG ACA AAC GGC CGC TTG CCG

670
         Val Lys Trp Met Ala Pro Glu Ala Leu Phe Asp Arg Ile Tyr Thr
         GTG AAG TGG ATG GCC CCG GAG GCT CTG TTC GAC CGA ATA TAC ACC
                     680                                    690
         His Gln Ser Asp Val Trp Ser Phe Gly Val Leu Leu Trp Glu Ile
    2321 CAT CAG AGT GAT GTT TGG TCC TTC GGT GTG CTG CTG TGG GAG ATC

700
         Phe Thr Leu Gly Gly Ser Pro Tyr Pro Gly Val Pro Val Glu Glu
         TTC ACG CTG GGC GGT TCG CCC TAC CCC GGC GTG CCC GTG GAG GAG
                     710                                    720
         Leu Phe Lys Leu Leu Lys Glu Gly His Arg Met Asp Lys Pro Ser
    2411 CTC TTC AAG CTG CTG AAG GAA GGC CAC AGG ATG GAC AAG CCC AGC

730
         Asn Cys Thr Asn Glu Leu Tyr Met Met Met Arg Asp Cys Trp His
         AAC TGC ACC AAC GAG CTG TAC ATG ATG ATG CGC GAC TGC TGG CAC
                     740                                    750
         Ala Val Pro Ser Gln Arg Pro Thr Phe Lys Gln Leu Val Glu Asp
    2501 GCC GTG CCC TCC CAG CGC CCC ACC TTC AAG CAG CTG GTG GAG GAC
                                      760
         Leu Asp Arg Ile Val Ala Met Thr Ser Asn Gln Glu Tyr Leu Asp
         CTG GAC AGG ATC GTG GCC ATG ACC TCC AAT CAG GAG TAC CTG GAC
                     770                                    780
         Leu Ser Val Pro Leu Asp Gln Tyr Ser Pro Gly Phe Pro Ala Thr
    2591 CTG TCG GTG CCG TTG GAT CAG TAC TCG CCC GGC TTC CCG GCC ACG

790
         Arg Ser Ser Thr Cys Ser Ser Gly Glu Asp Ser Val Phe Ser His
         CGC AGC TCC ACC TGC TCC TCG GGG GAG GAC TCG GTG TTC TCC CAC
                 800                                    810
         Asp Pro Leu Pro Asp Glu Pro Cys Leu Pro Arg Cys Pro Pro His
    2681 GAC CCG CTG CCC GAC GAG CCC TGC CTG CCG CGC TGC CCC CCG CAC
                                  819  OP
         Ser His Gly Ala Leu Lys Arg His TGA GGCTCCGCACGCAGCTGTGCCCCC
         AGC CAC GGA GCG CTG AAG CGG CAC
    2777 CCGGGCACCACCACCGCAGGGAACTGCCCAAAAGCTTTCGGCTGCTGTTGGGCTGTTGGT
         CGGCTCTTTTTTTTTTATCACCCATTTAAACCCTTCCCACGAGGTCTGTGCTTGGACATCC
    2897 CCACGTGGCGGTGCCGCCGTGTCCCTATGGGGCCGATGCGCGCTGTGAGCATCGCATCC
         CAGCGCTGCCCCAACCCACACGTGTGGGGTGTGCAGCACACGGGGCCGCCCCGGGGATCAG
    3017 CGCTAGGACAGAAGTGCCGTGTACATAGCTAAAATATGTATAAATATGAATATATATTT
         ACATGTCTTTTTAAAAGGGTGGTTACCAGAGCTGTGCCAGGCTGGTAGGGAGGTGCTGGTG
    3137 GCTGGTAGATATCAGTTGCTATATATAAAAAAAAA
```

| | | |
|---:|:---|---:|
| 1 | GCGGAACCCAAGGACTTTTCTCCGGTCCGAGCTCGGGGCGCC | 42 |
| 43 | CCGCACCGGGACGGTACCCGTGCTGCAGTCGGGCACGCCGCG | 84 |
| 85 | GGCCCGCCGGGGGCCTCCGCAGGGCGATGGAGCCGGTCTGCA | 126 |
| 127 | AGGAAAGTGAGGCGCCGCCGCTGCGTTCTGGAGGAGGGGGGC | 168 |
| 169 | ACAAGGTCTGGAGACCCCGGGTGGCGGACGGGAGCCCTCCCC | 210 |
| 211 | CCGCCCGCCTCCGGGGCACCAGCTCCGGCTCCATTGTTCCC | 252 |
| 253 | GCCCGGGCTGGAGGCGCCGAGCACCGAGCGCCGCCGGGAGTC | 294 |
| 295 | GAGCGCCGGCCGCGGAGGACTCTTGCGACCCCGCCAGGACCC | 336 |
| 337 | GAACAGAGCCCGGGGGCGGCGGGCCGGAGCCGGGGAGCCGGC | 378 |
| 379 | ACACGCCCGCTCGCACAAGCCACGGCGGACTCTCCCGAGGCG | 420 |
| 421 | GAACCTCCACGCCGAGCGAGGGTCAGTTTGAAAAGGAGGATC | 462 |
| 463 | GAGCTCACTGTGGAGTATCCATGGAGATGTGGAGCCTTGTCA | 504 |
| 505 | CCAACCTCTAACTGCAGAACTGGG ATG TGG AGC TGG AAG TGC | 546 |
| |                                         M   W   S   W   K   C | |
| 547 | CTC CTC TTC TGG GCT GTG CTG GTC ACA GCC ACA CTC TGC ACC | 588 |
| |  L   L   F   W   A   V   L   V   T   A   T   L   C   T | |
| 589 | GCT AGG CCG TCC CCG ACC TTG CCT GAA CAA GAT GCT CTC CCC | 630 |
| |  A   R   P   S   P   T   L   P   E   Q   D   A   L   P | |
| 631 | TCC TCG GAG GAT GAT GAT GAT GAT GAT GAC TCC TCT TCA GAG | 672 |
| |  S   S   E   D   D   D   D   D   D   D   S   S   S   E | |

Figure 4B

```
  673  GAGAAAGAAACAGATAACACCAAACCAAACCCCGTAGCTCCA  714
        E  K  E  T  D  N  T  K  P  N  P  V  A  P
  715  TATTGGACATCCCAGAAAAGATGGAAAAGAAATTGCATGCA   756
        Y  W  T  S  P  E  K  M  E  K  K  L  H  A
  757  GTGCCGGCTGCCAAGACAGTGAAGTTCAAATGCCCTTCCAGT  798
        V  P  A  A  K  T  V  K  F  K  C  P  S  S
  799  GGGACCCCAAACCCCACACTGCGCTGGTTGGAAAATGGCAAA  840
        G  T  P  N  P  T  L  R  W  L  E  N  G  K
  841  GAATTCAAACCTGACCACAGAATTGGAGGCTACAAGGTCCGT  882
        E  F  K  P  D  H  R  I  G  G  Y  K  V  R
  883  TATGCCACCTGGAGCATCATAATGGACTCTGTGGTGCCCTCT  924
        Y  A  T  W  S  I  I  M  D  S  V  V  P  S
  925  GACAAGGGCAACTACACCTGCATTGTGGAGAATGAGTACGGC  966
        D  K  G  N  Y  T  C  I  V  E  N  E  Y  G
  967  AGCATCAACCACACATACCAGCTGGATGTCGTGGAGCGGTCC 1008
        S  I  N  H  T  Y  Q  L  D  V  V  E  R  S
 1009  CCTCACCGGCCCATCCTGCAAGCAGGGTTGCCCGCCAACAAA 1050
        P  H  R  P  I  L  Q  A  G  L  P  A  N  K
 1051  ACAGTGGCCCTGGGTAGCAACGTGGAGTTCATGTGTAAGGTG 1092
        T  V  A  L  G  S  N  V  E  F  M  C  K  V
 1093  TACAGTGACCGGCAGCCGCACATCCAGTGGCTAAAGCACATC 1134
        Y  S  D  P  Q  P  H  I  Q  W  L  K  H  I
 1135  GAGGTGAATGGGAGCAAGATTGGCCCAGACAACCTGCCTTAT 1176
        E  V  N  G  S  K  I  G  P  D  N  L  P  Y
 1177  GTCCAGATCTTGAAGACTGCTGGAGTTAATACCACCGACAAA 1218
        V  Q  I  L  K  T  A  G  V  N  T  T  D  K
 1219  GAGATGGAGGTGCTTCACTTAAGAAATGTCTCCTTTGAGGAC 1260
        E  M  E  V  L  H  L  R  N  V  S  F  E  D
 1261  GCAGGGGACTATACGTGCTTGGCGGGTAACTCTATCGGACTC 1302
        A  G  E  Y  T  C  L  A  G  N  S  I  G  L
 1303  TCCCATCACTCTGCATGGTTGACCGTTCTGGAAGCCCTGGAA 1344
        S  H  H  S  A  W  L  T  V  L  E  A  L  E
 1345  GAGAGGCCGGCAGTGATGACCTCGCCCCTGTACCTGGAGATC 1386
        E  R  P  A  V  M  T  S  P  L  Y  L  E  I
 1387  ATCATCTATTGCACAGGGGCCTTCCTCATCTCCTGCATGGTG 1428
```

Figure 4C

```
                              290                                          300
         I  I  Y  C  T  G  A  F  L  I  S  C  M  V
                                              310
1429  GGGTCGGTCATCGTCTACAAGATGAAGAGTGGTACCAAGAAG              1470
         G  S  V  I  V  Y  K  M  K  S  G  T  K  K
                              320
1471  AGTGACTTCCACAGCCAGATGGCTGTGCACAAGCTGGCCAAG              1512
         S  D  F  H  S  Q  M  A  V  H  K  L  A  K
               330                              340
1513  AGCATCCCTCTGCGCAGACAGGTAACAGTGTCTGCTGACTCC              1554
         S  I  P  L  R  R  Q  V  T  V  S  A  D  S
                                   350
1555  AGTGCATCCATGAACTCTGGGGTTCTTCTGGTTCGGCCATCA              1596
         S  A  S  M  N  S  G  V  L  L  V  R  P  S
                     360                                 370
1597  CGGCTCTCCTCCAGTGGGACTCCCATGCTAGCAGGGGTCTCT              1638
         R  L  S  S  S  G  T  P  M  L  A  G  V  S
                                         380
1639  GAGTATGAGCTTCCCGAAGACCCTCGCTGGGAGCTGCCTCGG              1680
         E  Y  E  L  P  E  D  P  R  W  E  L  P  R
                           390
1681  GACAGACTGGTCTTAGGCAAACCCCTGGGAGAGGGCTGCTTT              1722
         D  R  L  V  L  G  K  P  L  G  E  G  C  F
               400                                    410
1723  GGGCAGGTGGTGTTGGCAGAGGCTATCGGGCTGGACAAGGAC              1764
         G  Q  V  V  L  A  E  A  I  G  L  D  K  D
                                    420
1765  AAACCCAACCGTGTGACCAAAGTGGCTGTGAAGATGTTGAAG              1806
         K  P  N  R  V  T  K  V  A  V  K  M  L  K
                     430                                       440
1807  TCGGACGCAACAGAGAAAGACTTGTCAGACCTGATCTCAGAA              1848
         S  D  A  T  E  K  D  L  S  D  L  I  S  E
                                         450
1849  ATGGAGATGATGAAGATGATCGGGAAGCATAAGAATATCATC              1890
         M  E  M  M  K  M  I  G  K  H  K  N  I  I
                                 460
1891  AACCTGCTGGGGGCCTGCACGCAGGATGGTCCCTTGTATGTC              1932
         N  L  L  G  A  C  T  Q  D  G  P  L  Y  V
                     470                                       480
1933  ATCGTGGAGTATGCCTCCAAGGGCAACCTGCGGGAGTACCTG              1974
         I  V  E  Y  A  S  K  G  N  L  R  E  Y  L
                                    490
1975  CAGGCCCGGAGGCCCCCAGGGCTGGAATACTGCTACAACCCC              2016
         Q  A  R  R  P  P  G  L  E  Y  C  Y  N  P
                     500                                       510
2017  AGCCACAACCCAGAGGAGCAGCTCTCCTCCAAGGACCTGGTG              2058
         S  H  N  P  E  E  Q  L  S  S  K  D  L  V
                                    520
2059  TCCTGCGCCTACCAGGTGGCCCGAGGCATGGAGTATCTGGCC              2100
         S  C  A  Y  Q  V  A  R  G  M  E  Y  L  A
                              530
2101  TCCAAGAAGTGCATACACCGAGACCTGGCAGCCAGGAATGTC              2142
         S  K  K  C  I  H  R  D  L  A  A  R  N  V
```

Figure 4D

```
            540                              550
2143  CTGGTGACAGAGGACAATGTGATGAAGATAGCAGACTTTGGC   2184
       L  V  T  E  D  N  V  M  K  I  A  D  F  G
                                    560
2185  CTCGCACGGGACATTCACCACATCGACTACTATAAAAGACA    2226
       L  A  R  D  I  H  H  I  D  Y  Y  K  K  T
            570                              580
2227  ACCAACGGCCGACTGCCTGTGAAGTGGATGGCACCCGAGGCA   2268
       T  N  G  R  L  P  V  K  W  M  A  P  E  A
                                    590
2269  TTATTTGACCGGATCTACACCCACCAGAGTGATGTGTGGTCT   2310
       L  F  D  R  I  Y  T  H  Q  S  D  V  W  S
                          600
2311  TTCGGGGTGCTCCTGTGGGAGATCTTCACTCTGGGCGGCTCC   2352
       F  G  V  L  L  W  E  I  F  T  L  G  G  S
            610                         620
2353  CCATACCCCGGTGTGCCTGTGGAGGAACTTTTCAAGCTGCTG   2394
       P  Y  P  G  V  P  V  E  E  L  F  K  L  L
                                630
2395  AAGGAGGGTCACCGCATGGACAAGCCCAGTAACTGCACCAAC   2436
       K  E  G  H  R  M  D  K  P  S  N  C  T  N
                      640                         650
2437  GAGCTGTACATGATGATGCGGGACTGCTGGCATGCAGTGCCC   2478
       E  L  Y  M  M  M  R  D  C  W  H  A  V  P
                                660
2479  TCACAGAGACCCACCTTCAAGCAGCTGGTGAAGACCTGGAC    2520
       S  Q  R  P  T  F  K  Q  L  V  E  D  L  D
                            670
2521  CGCATCGTGGCCTTGACCTCCAACCAGGAGTACCTGGACCTG   2562
       R  I  V  A  L  T  S  N  Q  E  Y  L  D  L
            680                         690
2563  TCCATGCCCCTGGACCAGTACTCCCCCAGCTTTCCCGACACC   2604
       S  M  P  L  D  Q  Y  S  P  S  F  P  D  T
                                  700
2605  CGGAGCTCTACGTGCTCCTCAGGGGAGGATTCCGTCTTCTCT   2646
       R  S  S  T  C  S  S  G  E  D  S  V  F  S
            710                              720
2647  CATGAGCCGCTGCCCGAGGAGCCCTGCCTGCCCCGACACCCA   2688
       H  E  P  L  P  E  E  P  C  L  P  R  H  P
                                  730
2689  GCCCAGCTTGCCAATGGCGGACTCAAACGCCGCTGACTGCCA.  2730
       A  Q  L  A  N  G  G  L  K  R  R  Z

2731  CCCACACGCCCTCCCCAGACTCCACCGTCAGCTGTAACCCTC   2772

2773  ACCCACAGCCCCTGCTGGGCCCACCACCTGTCCGTCCCTGTC   2814

2815  CCCTTTCCTGCTGGCAGGAGCCGGCTGCCTACCAGGGGCCTT   2856
```

Figure 4E

```
3613  GCTGGTGAGCAGGTCGCAAAGGA    3635
```

Figure 7A

```
CHICKEN FGFR  MFTWRCLILWAVLVTATLSAARPAPTLPDQALPKANIEVESHSAHPGDLLQLRCRLRDDVQSINWVRDGVQLPEN         75
h2            MWSWKCLLFWAVLVTATLCTARPSPTLPEQ-------------------------------------------         30
h3            MWSWKCLLFWAVLVTATLCTARPSPTLPEQ-------------------------------------------         30
h4            MWSWKCLLFWAVLVTATLCTARPSPTLPEQ-------------------------------------------         30
h5            MWSWKCLLFWAVLVTATLCTARPSPTLPEQ-------------------------------------------         30

NRTRITGEEVEVRDRVPEDSGLYACMTNSPSGSETTYFSVNVSDALPSAEDDDDEDDSSSEEKEADNTKPNQ-AV        149
              ----------------------------DALPSSEDDDDDDDSSSEEKETDNTKPNRMPV                       62
              ----------------------------DALPSSEDDDDDDDSSSEEKETDNTKPN--PV                       60
              ----------------------------DALPSSEDDDDDDDSSSEEKETDNTKPNRMPV                       62
              ----------------------------DALPSSEDDDDDDDSSSEEKETDNTKPN--PV                       60

APYWTYPEKMEKKLHAVPAAKTVKFKCPSGGTPNPTLRWLKNGKEFKPDHRIGGYKVRYATWSIIMDSVVPSDKG        224
              APYWTSPEKMEKKLHAVPAAKTVKFKCPSSGTPNPTLRWLKNGKEFKPDHRIGGYKVRYATWSIIMDSVVPSDKG        137
              APYWTSPEKMEKKLHAVPAAKTVKFKCPSSGTPNPTLRWLKNGKEFKPDHRIGGYKVRYATWSIIMDSVVPSDKG        135
              APYWTSPEKMEKKLHAVPAAKTVKFKCPSSGTPNPTLRWLENGKEFKPDHRIGGYKVRYATWSIIMDSVVPSDKG        137
              APYWTSPEKMEKKLHAVPAAKTVKFKCPSSGTPNPTLRWLKNGKEFKPDHRIGGYKVRYATWSIIMDSVVPSDKG        135

NYTCIVENKYGSINHTYQLDVVERSPHRPILQAGLPANKTVALGSNVEFVCKVYSDPQPHIQWLKHIEVNGSKIG        299
              NYTCIVENEYGSINHTYQLDVVERSPHRPILQAGLPANKTVALGSNVEFMCKVYSDPQPHIQWLKHIEVNGSKIG        212
              NYTCIVENEYGSINHTYQLDVVERSPHRPILQAGLPANKTVALGSNVEFMCKVYSDPQPHIQWLKHIEVNGSKIG        210
              NYTCIVENEYGSINHTYQLDVVERSPHRPILQAGLPANKTVALGSNVEFMCKVYSDPQPHIQWLKHIEVNGSKIG        212
              NYTCIVENEYGSINHTYQLDVVERSPHRPILQAGLPANKTVALGSNVEFMCKVYSDPQPHIQWLKHIEVNGSKIG        210
```

```
PDNLPYVQILKTAGVNTTDKEMEVLHLRNVSFEDAGEYTCLAGNSIGISHHSAWLTVLEATEQSPAMMTSPLYLE    374
PDNLPYVQILKTAGVNTTDKEMEVLHLRNVSFEDAGEYTCLAGNSIGLSHHSAWLTVLEALEERPAVMTSPLYLE    287
PDNLPYVQILKTAGVNTTDKEMEVLHLRNVSFEDAGEYTCLAGNSIGLSHHSAWLTVLEALEERPAVMTSPLYLE    285
PDNLPYVQILKVIMAPVFVGQSTGKETTVSGAQVPVGRLSCPRMGSFLTLQAHTLHLSRDLATISPRTSNRGHKVE   287
PDNLPYVQILKVIMAPVFVGQSTGKEITVSGAQVPVGRLSCPRMGSFLTLQAHILHLSRDLATISPRISNRGHKVE   285

IIIYCTGAFLISCMVVTVIIYKMKSTTKKTDFNSQLAVHKLAKSIPLRRQVTVSADSSSSMNSGVMLVRPSRLSS    449
IIIYCTGAFLISCMVVTVIIVYKMKSGTKKSDFHSQMAVHKLAKSIPLRRQVTVSADSSASMNSGVLLVRPSRLSS   362
IIIYCTGAFLISCMVVTVIIVYKMKSGTKKSDFHSQMAVHKLAKSIPLRRQVTVSADSSASMNSGVLLVRPSRLSS   360
VSWEQRAIAGNGGAGL*                                                              302
VSWEQRAIAGNGGAGL*                                                              300

SGTPMLAGVSEYELPEDPRWELPRDRLILGKPLGEGCFGQVVLAEAIGLDKDKPNRVTKVAVKMLKSDATEKDLS    524
SGTPMLAGVSEYELPEDPRWELPRDRLVLGKPLGEGCFGQVVLAEAIGLDKDKPNRVTKVAVKMLKSDATEKDLS    437
SGTPMLAGVSEYELPEDPRWELPRDRLVLGKPLGEGCFGQVVLAEAIGLDKDKPNRVTKVAVKMLKSDATEKDLS    435

DLISEMEMMKMIGKHKNIINLLGACTQDGPLYVIVEYASKGNLREYLQARRPPGMEYCYNPTRIPEEQLSFKDLV    599
DLISEMEMMKMIGKHKNIINLLGACTQDGPLYVIVEYASKGNLREYLQARRPPGLEYCYNPSHNPEEQLSSKDLV    512
DLISEMEMMKMIGKHKNIINLLGACTQDGPLYVIVEYASKGNLREYLQARRPPGLEYCYNPSHNPEEQLSSKDLV    510

SCAYQVARGMEYLASKKCIHRDLAARNVLVTEDNVMKIADFGLARDIHHIDYYKKTTNGRLPVKWMAPEALFDRI    674
SCAYQVARGMEYLASKKCIHRDLAARNVLVTEDNVMKIADFGLARDIHHIDYYKKTTNGRLPVKWMAPEALFDRI    587
SCAYQVARGMEYLASKKCIHRDLAARNVLVTEDNVMKIADFGLARDIHHIDYYKKTTNGRLPVKWMAPEALFDRI    585

YTHQSDVWSFGVLLWEIFTLGGSPYPGVPVEELFKLLKEGHRMDKPSNCTNELYMMMRDCWHAVPSQRPTFKQLV   749
YTHQSDVWSFGVLLWEIFTLGGSPYPGVPVEELFKLLKEGHRMDKPSNCTNELYMMMRDCWHAVPSQRPTFKQLV   662
YTHQSDVWSFGVLLWEIFTLGGSPYPGVPVEELFKLLKEGHRMDKPSNCTNELYMMMRDCWHAVPSQRPTFKQLV   660

EDLDRIVAMTSNQEYLDLSVPLDQYSPGFPATRSSTCSSGEDSVFSHDPLPDEPCLPRCPPHSHGALKRH*       819
EDLDRIVALITSNQEYLDLSMPLDQYSPSFPDTRSSTCSSGEDSVFSHEPLPEEPCLPRIPAQLANGGLKRR*     733
EDLDRIVALITSNQEYLDLSMPLDQYSPSFPDTRSSTCSSGEDSVFSHEPLPEEPCLPRIHPAQLANGGLKRR*    731
```

```
1 c1 FGFR cDNA
2 HUMAN FGFR GENOMIC SEQUENCE (AMINO ACID)
3 HUMAN FGFR GENOMIC SEQUENCE (NUCLEOTIDE)
4 h2 FGFR cDNA

1 M F T W R G L I L W A V L V T A T L S A A R P A P
2 - - - - - - - - - - - - - - - - - - - - - - - -
3 - - - - - - - - - - - - - - - - - - - - - - - -
4 M W S W K C L L F W A V L V T A T L C T A R P S P

1 T L P D Q A L P K A N - E V E S H S A H P G D L L
2 - - - - - - - - - - - - - - - - - - - - - - - -
3 - - - - - - - - - - - - - - - - - - - - - - - -
4 - - - - - - - - - - - - - - - - - - - - - - - -

1 Q L R G R L R D D V Q S I N W V R D G V Q L P E N
2 - - - - - - - - - - - - - - - - - - - - A E S
3                                         GTGCAGCTGGCGGAAAGC
4 - - - - - - - - - - - - - - - - - - - - - - - -

1 N R T R I I G P G S D T Y F S V N V S - - - - - D
2 - - - - - - - - - - - - - - - - - - - - - - - -
3 AACCGCACCCGCATCACAGAGGGGAGGAGGTGGAGGACTCCGTGCCCGAGACTCCGGCCTCTATGCTTGC
4 M T S S P S G S D T T Y F S V N V S / 1 KB INTRON / D

1 M T S S P S G S D T T Y F S V N V S - - - - - D
2 - - - - - - - - - - - - - - - - - - - - - - -
3 GTAACCAGGAGCCCCTCGGGCAGTGACACCACCTACTTCTCGGTCAATGTTTCAG/GTTGGT....CCATAG/AT
4 - - - - - - - - - - - - - - - - - - - - - - D

1 A L P S A E D D D D D D D D S S E D
2 A L P S S E D D D D D D D D D D E D
3 CTCTCCCTCCTCGGAGGATGATGATGATGATGAT
4 A L P S S E D D D D D D D D D
```

RECEPTORS FOR FIBROBLAST GROWTH FACTORS

This application is a Division of application Ser. No. 07/834,311 filed Feb. 13, 1992, the U.S. National Phase of PCT/US90/03830, filed Jul. 6 1990, which is a continuation-in-part application of commonly assigned patent application U.S.S.N. 07/377,003 filed on July 6, 1989, now abandoned which is hereby incorporated herein by reference.

This invention was made in part with government support under grant contract No. HL-07192 and under grants RO1 HL-32898 and P01 HL-43821-01, all awarded by the National Institutes of Health. The government may have certain rights in this invention.

FIELD OF THE INVENTION

The present invention relates to receptors for growth factors, specifically to the fibroblast growth factor receptor (FGF-R). More particularly, it provides various purified fibroblast growth factor receptor proteins, nucleic acids encoding the receptor proteins, methods for the production of purified FGF-R proteins, proteins made by these methods, antibodies against these proteins, and diagnostic and therapeutic uses of these various reagents.

BACKGROUND OF THE INVENTION

Polypeptide growth factors are mitogens that act on cells by specifically binding to receptors situated at the plasma membrane. These receptors usually have three major identifiable regions. The first is an extracellular region which contains the domain that binds the polypeptide growth factor (i.e. the ligand-binding domain). The second region is a transmembrane region and the third is an intracellular region. Many of these receptors contain a tyrosine kinase domain in the intracellular region.

The fibroblast growth factor receptor (FGF-R) proteins bind to a family of related growth factor ligands, the fibroblast growth factor (FGF) family. This family of growth factors are characterized by amino acid sequence homology, heparin-binding avidity, the ability to promote angiogenesis and mitogenic activity toward cells of epithelial, mesenchymal and neural origin.

The FGF family includes the following seven known FGFs:

(1, 2) acidic FGF (aFGF) and basic FGF (bFGF) (D. Gospodarowicz et al., *Mol. Cell. Endocrinol.*, 46:107 (1986);

(3) the int-2 gene product (R. Moore et al., *EMBO. J.*, 5:919 (1986);

(4) the hst gene product or Kaposi's sarcoma FGF (K. J. Anderson et al. *Nature*, 332:360 (1988); M. Taira et al., *Proc. Natl. Acad. Sci. USA*, 84:2980 (1987));

(5) FGF-5 (X. Zhan et al., *Mol. Cell. Biol.*, 8:3487 (1988)); and (6) keratinocyte growth factor (J. S. Rubin et al., *Proc. Natl. Acad. Sci. USA*, 86:802 (1989)).

(7) FGF-6 (I. Marics, et al., *Oncogene* 3:335 (1989)).

The actions of acidic and basic FGF are mediated through binding to high affinity cell surface receptors of approximately 145 and 125 kDa (G. Neufeld and D. Gospodarowicz, *J. Biol. Chem.*, 261:5631 (1986)).

The reference of Imamura et al., "Purification of Basic FGF Receptors from Rat Brain," *Biochem. Biophys. Res. Communications*, 155:583 (Sep. 15, 1988) discloses the purification of nanogram amounts of a basic FGF receptor (bFGF-R) from rat brain.

While genes encoding a number of growth factor receptors have been molecularly cloned (e.g., mouse PDGF receptor, Yarden et al., *Nature*, 323:226 (1986), no clone has previously been identified as encoding a fibroblast growth factor receptor (FGF-R). Using antiphosphotyrosine antibodies to screen λgt11 cDNA expression libraries, a 2.5 kilobase cDNA encoding a novel tyrosine kinase gene, designated bek (bacterially expressed kinase), was isolated from a mouse liver cDNA library. (S. Kornbluth et al., "Novel Tyrosine Kinase Identified by Phosphotyrosine Antibody Screening of cDNA Libraries", *Mol. Cell. Biol.* No. 8, 541 (1988)). The bek sequence did not contain a transmembrane region and therefore could not be identified as a growth factor receptor. Another protein tyrosine kinase gene designated flg (fms-like-gene) was isolated from a human endothelial cell cDNA library by hybridization under relaxed stringency with a v-fms oncogene probe. (M. Ruta et al., "A Novel Protein Tyrosine Kinase Gene Whose Expression is Modulated During Endothelial Cell Differentiation", Oncogene, 3:9 (1988)). Those authors could not identify a transmembrane region in their isolated sequence and therefore hypothesized that flg encodes a cytoplasmic tyrosine kinase.

The purified and cloned chicken bFGF and human bFGF receptors of this invention have amino acid sequence similarity with the bek and flg clones in the regions which have been isolated. However, both the bek and flg sequences reported were incomplete and there was no recognition of their function as FGF binding receptors. Moreover, the prior reports failed to recognize many of the structural and functional features described in the present invention.

Members of the FGF family appear to have roles in tissue development, tissue repair, maintenance of neurons and in the pathogenesis of disease. Aberrant expression of FGF may cause cell transformation by an autocrine mechanism. Moreover, FGFs may enhance tumor growth and invasiveness by stimulating blood vessel growth in the tumor or by inducing production of proteins such as plasminogen activator. However, identification of the components involved and understanding of the mechanisms and interactions involved remain woefully incomplete.

Purified FGF receptors and fragments, and isolated DNA sequences encoding defined FGF receptors and defined fragments (e.g., the ligand-binding domain) will greatly accelerate the understanding of fibroblast growth factor functions. Antibodies against specific and defined regions of the FGF receptor also become available. These reagents will find both diagnostic and therapeutic uses in the aforementioned processes. The present invention fulfills these and other needs.

SUMMARY OF THE INVENTION

The present invention provides purified fibroblast growth factor receptor (FGF-R) proteins, nucleic acids encoding FGF-R proteins, methods for the production of purified FGF-R proteins, purified proteins made by these methods, antibodies against these proteins and fragments, and diagnostic and therapeutic uses of these reagents. Notably, the present invention provides soluble and secreted forms of the receptors exhibiting an unusual receptor structure.

The present invention provides a method for modifying in vivo a fibroblast growth factor receptor modulated activity comprising administering to a patient an amount of a fibroblast growth factor receptor blocking agent effective to inhibit fibroblast growth factor binding to said fibroblast growth factor receptor. Typically, the agent will be a fragment of a human fibroblast growth factor receptor, e.g., a fragment produced in a cell transformed with a nucleic acid containing at least about 15 bases of a sequence selected from the group consisting of:

a) a DNA sequence in FIGS. 3 or 4;
b) a sequence encoding a polypeptide of FIGS. 3, 4 or 7; and
c) a sequence substantially homologous to a sequence of FIGS. 3 or 4.

The fragment will often be a fibroblast growth factor receptor extracellular domain without a tyrosine kinase region.

Alternatively, a method is provided for inhibiting binding between a fibroblast growth factor and a fibroblast growth factor receptor in a solution. This method will contain a step of combining an FGF-R peptide, e.g., a peptide homologous in sequence to a sequence described in FIGS. 3, 4 or 7 to a solution or medium containing fibroblast growth factor and fibroblast growth factor receptor, usually native fibroblast growth factor receptor. Such methods will be useful in vitro, after employing labeled FGF-R peptide in assay procedures.

Compositions containing a soluble FGF-R polypeptide having between about five and two hundred contiguous amino acids from a human FGF-R extracellular domain are described. In one embodiment, the polypeptide contains at least about 80 amino acids from residues 1 to 287 of a human fibroblast growth factor receptor of FIG. 7 or an IgII or IgIII domain, or both. In alternative embodiments, the IgII domain will have about 7 contiguous amino acids from residues 85 to 141 of a human sequence of FIG. 7 or may contain a carboxy-terminal sequence substantially homologous to the 79 amino acid sequence from residues 222 to 300 of a soluble human protein of FIG. 7. Particularly preferred polypeptides consist essentially of the h4 or h5 sequences (FIG. 7).

A further aspect of the invention is a fibroblast growth factor receptor composition containing a substantially pure polypeptide of less than about 85 KDa comprising a fibroblast growth factor-binding domain. The polypeptide may be soluble or may specifically possess a signal segment, an IgI segment, an acidic segment, an IgII segment, an IgIII segment, an IgIIIT segment, or a transmembrane segment. Preferred embodiments will be homologous to a sequence described in FIGS. 3, 4 or 7 or will include at least about 30 amino acids of each of both IgII and IgIII domains. The polypeptide can be one polypeptide chain in a multi-chain complex of proteins. A chicken fibroblast growth factor receptor is one preferred embodiment.

The present invention embraces isolated nucleic acids encoding human fibroblast growth factor receptor proteins which substantially lack an intracellular domain. Such a nucleic acid will usually exhibit a sequence homologous to an IgII domain described in FIG. 7, or may include a substantially full length IgII domain. The nucleic acid will usually also have a signal segment, an IgI segment, an acidic segment, an IgIII segment, an IgIIIT segment, a transmembrane segment, or a tyrosine kinase segment, and will preferably correspond to a sequence described in FIGS. 3, 4 or 9. A particularly preferred embodiment is a nucleic acid encoding a receptor native to a human. The nucleic acids may be operably linked to a transcription promoter sequence and may further be incorporated into expression vectors suitable for production of recombinant FGF-R peptide.

Also included are isolated nucleic acids encoding a soluble human fibroblast growth factor receptor, preferably one homologous to h4 or h5. Protein products made by expressing such an isolated nucleic acid are provided.

A method is provided for making these proteins of newly recognized utility, e.g., fibroblast growth factor receptor activity, said method comprising expressing an isolated nucleic acid. Products produced by this method are now also available.

Additional methods are provided for making fibroblast growth factor receptor peptides by transforming a cell with a nucleic acid of at least about 21 bases of a sequence selected from the group consisting of:

a) a DNA sequence in FIGS. 3, 4 or 9;
b) a sequence encoding a polypeptide of FIGS. 3, 4 or 7; and
c) a sequence substantially homologous to a sequence of FIGS. 3, 4 or 9.

Other methods for producing an antibody against a fibroblast growth factor receptor fragment are described, including a step of producing an antibody against a polypeptide epitope homologous to a sequence of at least six contiguous amino acids described in FIGS. 3, 4 or 7. The epitopes of most interest will be those from a signal segment, an IgI segment, an acidic segment, an IgII segment, an IgIII segment, or an IgIIIT segment.

As a diagnostic use, these reagents provide a method for measuring a fibroblast growth factor or a fibroblast growth factor receptor in a target sample, said method comprising the steps of:

combining said target sample with a fibroblast growth factor receptor segment; and determining the extent of binding between said segment and said sample.

This invention also provides a transformed cell capable of expressing a polypeptide homologous to at least a portion of a human fibroblast growth factor receptor. A preferred embodiment is where the cell expresses a polypeptide homologous to substantially the entire membrane bound or soluble form of a human fibroblast growth factor receptor.

BRIEF DESCRIPTION OF THE DRAWINGS

FIG. 1 compares the binding of various derivatives of FGF to FGF-R.

FIG. 2(A) is an autoradiograph of cross-linked chicken membrane fractions and WGA eluates subjected to gel electrophoresis. FIG. 2(B) is a silver stained gel showing pure FGF receptor resulting from an affinity purification performed on the WGA-Sepharose 4B column chicken embryo eluate shown in FIG. 2(A).

FIGS. 3A, B, C and D shows the nucleotide and amino acid sequence of a chicken bFGF receptor.

FIGS. 4A, B, C, D, and E show the nucleotide and amino acid sequence of a human FGF receptor.

FIGS. 7A and B provides an amino acid sequence comparison of various different FGF receptor forms. The amino acid sequences of 4 human receptor forms are shown in comparison to a chicken FGF receptor sequence. Sequences which differ from the chicken FGF receptor sequence are outlined in open boxes. Transmembrane sequences are underlined. These DNA sequences are in GenBank/EMBL data bases under the following accession numbers: h2 is M34185, h3 is M34186, h4 is M34187, and h5 is M34188.

FIG. 9 presents a comparison of various human FGF receptor genomic sequences with deduced amino acid sequences of FGF receptor cDNA clones. The sequence of a human genomic fragment obtained by PCR is shown in comparison to human and chicken cDNA sequences. A 1 kb intron separates genomic sequences encoding the Ig-like (Ig) domain and the highly acidic region. Dashed lines represent continuous sequence with no gaps. The deduced amino acid sequence shown for the chicken FGF receptor begins with the initiator methionine residue (1) and ends with the acidic region (EDDDDEDD; amino acids 125–132 in c1 FGF-R). The amino acid sequence shown for the human h2 FGF receptor begins with the initiator methionine residue (1) and ends with the acidic region (EDDDDDDD; amino acids 37–44 in h2).

DETAILED DESCRIPTION OF THE PREFERRED EMBODIMENT

OUTLINE

I. General Description

Figure 1A:
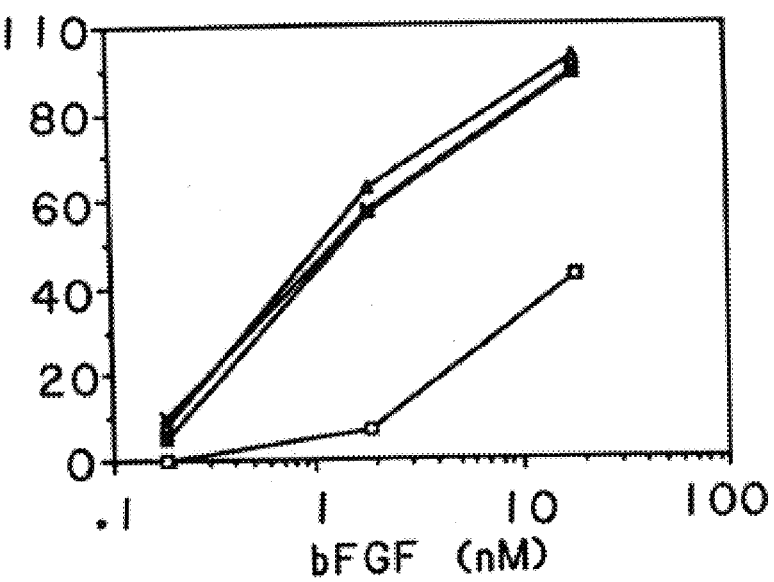
FIG. 1(A) is a graph showing the percent binding inhibition of $^{125}$I-labeled bFGF.

A. FGF-R
   1. structural features
      a. extracellular domain i. signal sequence ii. Ig domains iii. acidic amino acid region
      b. transmembrane segment
      c. intracellular domain i. tyrosine kinase ii. insert
   2. function
      a. bind FGF
      b. bind to FGF-R peptide
      c. tyrosine kinase activity B. Physiological Functions
   1. cellular
   2. tissue differentiation
   3. organismal II. Polypeptides A. Soluble Forms B. Truncated Forms C. Fusion Proteins D. Genetic Variants (site-directed mutagenesis)

E. Compositions Comprising Proteins

III. Nucleic Acids

A. Isolated Nucleic Acids

B. Recombinant Nucleic Acids

C. Compositions Comprising Nucleic Acids

IV. Methods for Making FGF-R

A. Protein Purification
   1. affinity with derivatized FGF
   2. various ligands, same receptor B. Expression of Nucleic Acids V. Antibodies VI. Methods for Use A. Diagnostic B. Therapeutic

I. General Description

A first aspect of the invention provides homogeneous FGF-R peptides. These homogeneous FGF-Rs include a chicken basic fibroblast growth factor receptor and various human fibroblast growth factor receptors. Homogeneous polypeptides either having FGF-R ligand-binding activity or comprising a portion of the ligand-binding domain of an FGF-R are described. Notably, the present invention provides homogeneous polypeptides corresponding to naturally occurring FGF-binding proteins having unexpected structural features. One class provides soluble proteins lacking a transmembrane segment, another class provides proteins possessing both a transmembrane segment and a tyrosine kinase domain. Both of these classes have an unexpected extracellular domain structure shorter than the corresponding chicken FGF-R. Experimental data indicating that a single receptor binds various FGF types is also described.

A second aspect of the invention provides isolated DNA sequences. These sequences encode polypeptides having FGF-R ligand-binding activity, including polypeptides which correspond to naturally occurring full-length fibroblast growth factor receptors. DNA sequences encoding a chicken bFGF-R or encoding various human FGF-Rs (hFGF-R) have been isolated. Also provided are cloning and expression vehicles containing the FGF-R encoding sequences. A DNA sequence encoding the full-length FGF receptor or an FGF-R polypeptide fragment can be operably linked to control sequences and expressed in a culture of a compatible transformed, transfected or infected host cells.

Methods of synthesizing growth factor receptor proteins and methods for providing analogues of the fibroblast growth factor receptors are provided.

The invention also provides antibodies to defined domains of the receptor. Still further aspects of the invention include methods for evaluating compositions which are agonistic or antagonistic to ligand and receptor interactions, particularly those which promote or inhibit binding interactions.

Diagnostic and therapeutic uses for the reagents provided herein are also described.

A. FGF Receptors

The fibroblast growth factor receptors (FGF-R) are receptors for the family of fibroblast growth factors (FGFs), as described above. See also P. L. Lee et al., *Science* 245:57–60, (1989), which is hereby incorporated herein by reference.

The FGF family consists of polypeptide growth factors characterized by amino acid sequence homology, heparin-binding avidity, the ability to promote angiogenesis, and mitogenic activity toward cells of epithelial, mesenchymal, and neural origin. The FGF family includes acidic FGF, basic FGF, the int-2 gene product, the hst gene product (Kaposi sarcoma-FGF), FGF-5, the keratinocyte growth factor, and FGF-6. Members of the FGF family appear to have roles in development, tissue repair, maintenance of neurons, and the pathogenesis of disease. Aberrant expression of FGFs may cause cell transformation by an autocrine mechanism. Moreover, FGFs may enhance tumor growth and invasiveness by stimulating blood vessel growth into the tumor or by inducing production of proteases such as plasminogen activator.

The term "ligand" refers to the molecules, usually members of the fibroblast growth factor family, that bind the domains involved in the growth factor binding. Also, a ligand is a molecule which serves either as the natural ligand to which the receptor binds, or a functional analogue which may serve as an agonist or antagonist.

As described herein, a chicken bFGF receptor is characterized by various identifiable structural features. The chicken and human FGF-R structures are generalized to define a structural nomenclature applicable to other FGF-Rs. General descriptions of protein structure and its relationship to nucleic acid sequences are discussed in J. D. Watson et al., *Molecular Biology of the Gene*, 4th Ed., vols. 1 and 2, Benjamin/Cummings, Menlo Park, Calif., (1987); and B. Alberts et al., *Molecular Biology of the Cell*, 2d Ed., Garland, N.Y., (1989), each of which is incorporated herein by reference. Common structural features of known FGF-Rs are described, including various naturally occurring soluble human FGF binding proteins. A human fibroblast growth factor receptor is a protein either derived from a natural human FGF-R gene, or which shares significant structural characteristics peculiar to a naturally occurring human receptor for FGF.

The isolated full-length chicken FGF-R mRNA contains a single hydrophobic segment similar to a membrane-spanning segment (designated the transmembrane segment). The segments of FGF-R amino-proximal to the transmembrane segment are designated the extracellular domain, while the segments carboxy-proximal to the transmembrane segment are designated the intracellular domain. From the amino-terminus, the extracellular domain has an $NH_2$-terminal hydrophobic putative signal sequence, an immunoglobulin-like domain (designated IgI), and acidic segment, a second immunoglobulin-like domain (designated IgII), and a third immunoglobulin-like domain (designated IgIII). Although various structured features may be identified in the external domain of the FGF-R, the most important functional property which defines the domain is the binding to the receptor ligands, e.g., members of the FGF family. As discussed below, this function is correlated with the combined presence of IgII and IgIII domains.

The intracellular domain is characterized by the presence of a split tyrosine kinase structural domain and, in the chicken receptor, is about 424 residues long. Functionally, this domain is defined by its tyrosine kinase activity, typically modulated by ligand binding to the extracellular domain. A protein substantially lacks an intracellular domain when it lacks a prototypical intracellular domain, particularly lacking a tyrosine kinase domain.

Besides the chicken receptor, four unique human cDNA clones have been identified. These encode previously unknown FGF receptor variants which contain only two Ig-like domains. Two of the human clones encode membrane spanning receptors and two encode putative secreted forms. Both the forms exhibiting the 3 Ig-like or 2 Ig-like domain structures mediate biological responsiveness to acidic and basic FGF. Thus, the first Ig domain of the 3 Ig domain form may have a function other than binding of acidic and basic FGF. The multiple human receptor forms, are identical in some regions but are highly divergent in other selected regions of the extracellular domain. Two of the human variant receptors, h4 and h5, are likely to encode a secreted form of the FGF receptor.

A typical FGF-R nucleic acid sequence encodes a transitory NH 2-terminal hydrophobic sequence, which is usually cleaved during the translocation process. The classical function of a signal sequence is to direct the nascent polypeptide chain to membrane bound ribosomes, thereby leading to membrane translocation. However, since the signal sequence is typically removed in the translocation process, the signal sequence is absent in a mature polypeptide.

The Ig-like domains (Ig domains) are characterized by three main features: (i) the presence of two characteristic cysteine residues in each domain; (ii) the presence of a consensus tryptophan residue 11 to 12 amino acids on the COOH-terminal side of the first cysteine residue in each Ig-like domain; and (iii) the presence of the consensus sequence, DXGXYXC, on the $NH_2$-terminal side of the second cysteine residue. The last feature is modified in the cases of the soluble receptor proteins, and substituted with an equivalently sized sequence.

Figure 6:
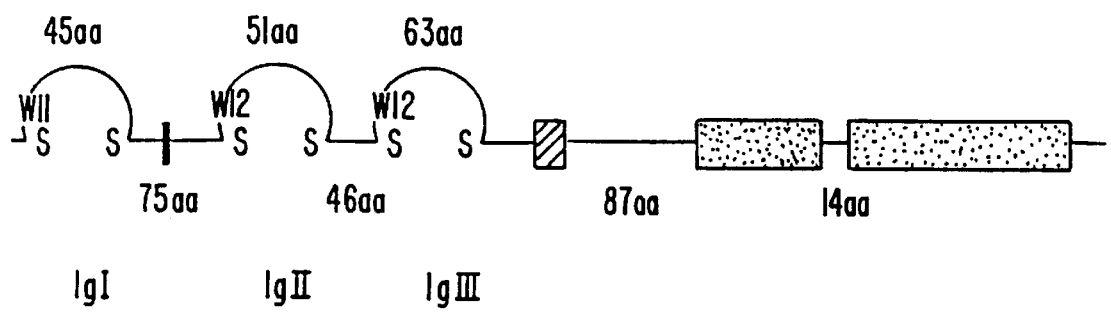
FIG. 6 is a schematic of a chicken bFGF receptor indicating the (solid block) acidic domain; (cross-hatched block) transmembrane region; (flecked block) tyrosine kinase domain; (S), position of the SH cysteine residues (in contrast to the S designation of Table I); (W), position of tryptophan residue with respect to the first cysteine residue in the Ig-like domain.

Additional features characteristic of the Ig domains are apparent both in comparing the domains with one another, and comparing homologous domains of different receptor molecules. The amino-proximal Ig domain found in the chicken clone was designated IgI. As the chicken clone has three Ig domains, the domains have been numbered from the amino terminus. As indicated in FIG. 6, the IgI domain includes the 45 amino acids flanked by a pair of cysteine residues. The chicken IgI domain has a high homology in sequence with the IgI domain found in the genomic sequence of the human FGF-R. However, the human forms appear to lack a domain corresponding to IgI.

The next Ig domain is designated IgII, and in the chicken receptor includes 51 amino acids between the two cysteine residues (see FIGS. 3 and 6). As described below, this domain, in combination with the IgIII domain is involved with ligand binding. The polypeptide sequence homology of this domain between the chicken and human receptors is quite high, as shown by the sequence alignments in FIG. 7. It will be noted that the human receptors lack an Ig I domain but have IgII and IgIII domains. The cysteine residues used to delineate this domain are residues 176, 89, 87, 89, and 87 on the amino proximal side, and 228, 141, 139, 141, and 139 on the carboxy proximal side for the chicken, h2, h3, h4 and h5 receptors, respectively.

The third Ig domain is designated IgIII and in the chicken receptor includes 63 amino acids between the two cysteine residues. See FIGS. 3 and 6. Again, although the human receptors have only two domains, the domains correspond to IgII and IgIII. In both the chicken and human forms, the IgIII domain is that closest to the transmembrane segment. The cysteine residues for the chicken, h2, h3, h4 and h5 receptors, respectively, used to delineate this domain are residues 274, 187, 185, 187, and 185 on the amino proximal side and residues 339, 252, 250, 253, and 251 on the carboxy proximal side.

The h4 and h5 soluble receptors have a substituted terminal segment designated IgIIIT. This segment is a substituted terminal segment replacing part of the membrane bound to IgIII, and is 79 amino acids long. This sequence corresponds to amino acids 224 and 222 of h4 and h5, respectively, while preserving many of the features found in the IgIII domain except of the DSGSYSC. It should be noted, however, the IgIIIT sequences are conserved between the soluble forms of the human FGF-R.

Between the first and second immunoglobulin-like domains, the FGF receptors (shown for the basic FGF-R, but the same FGF-R binds both the acidic and basic FGFS) have a feature not found in other members of the immunoglobulin superfamily. There is a series of eight consecutive acidic residues (EDDDDEDD in the case of chicken, and EDDDDDDD in the case of human) followed by three serine residues and two additional acidic residues (FIGS. 3 and 7). Although uninterrupted stretches of 7 to 35 acidic residues have been described for several intracellular proteins, in particular nuclear proteins, such acidic regions are unusual in the extracellular region of transmembrane receptor proteins.

The 5 receptor species (e.g. the chicken, h2, h3, h4 and h5 forms) also exhibit variability at a specific location between the conserved acidic region and the conserved second Ig-like domain (IgII). The h2 and h4 receptor forms contain two amino acids (ArgMet) at positions 59 and 60, while the chicken receptor contains a single amino acid (Asn) at this position and the h3 and h5 receptor forms contain no corresponding amino acids at this position (see asterisks, FIG. 8).

Another unusual feature is the length of the juxtamembrane region, the region between the membrane spanning segment and the kinase domain. This region is normally conserved among receptor tyrosine kinases. For example, the juxtamembrane region is consistently 49 to 51 residues in length in the receptors for PDGF, CSF-1, epidermal growth factor (EGF), human epidermal growth factor-2 (HER2) and insulin. The FGF receptors with an intercellular domain have an unusually long juxtamembrane region of about 87 residues.

The cytoplasmic regions of the amino acid sequences are about 424 and 425 residues long, respectively for the chicken and human forms. These also contain a tyrosine kinase sequence (about residues 482 to 759, 395 to 672, and 393 to 670, respectively for the chicken, h2, and h3 forms). Overall, the kinase region of the bFGF receptors shares the most sequence identity (about 51 to 53%) with the PDGF and CSF-1 receptors. The bFGF receptors contain the GXGXXG motif and the conserved lysine residue (about residue 512) that form part of the adenosine 5'-triphosphate (ATP) binding site of tyrosine kinases. The bFGF receptors also contain the two characteristic tyrosine kinase motifs, HRDLAARNVL and DFGLAR, and a tyrosine (about residues 651, 564 and 562) at the position analogous to the major phosphorylation site of $pp60^{v-src}$ (about Tyr 416).

The kinase coding sequence of the bFGF receptors, defined by homology to other tyrosine kinases, are split by an insertion of 14 amino acids. The length of the insertion in the kinase region is shorter than that found in the receptors for PDGF and CSF-1 (104 and 70 amino acids, respectively) and is similar to the length of the inserted sequence in the receptors for insulin and insulin-like growth factor-I.

The FGF-R appears to have three different biological functions. The first is the binding of ligands, usually the FGF proteins or their analogues. These ligands or analogues may also serve as either agonists or antagonists. The ligand binding site is apparently in the extracellular domain. The receptor transduces a signal in response to ligand binding, and the result is a ligand modulated activity. As the likely ligand is a FGF, the signal will ordinarily be FGF-modulated.

A second biological activity relates to the tyrosine kinase enzymatic activity. This activity is typically activated in response to ligand binding. However, since the receptors are likely to function in a dimer state, the intrachain binding interactions may be considered another biological activity which may be mediated by blocking agents. this may serve as an additional means to modulate FGF-mediation of particular activities.

B. Physiological Implications

The interactions of FGFs with their receptors cause changes in, on particular cell types, cell morphology and cell transformation, cell proliferation, cell differentiation, cell senescence, heparin sensitivity, and heparin effects. The in vivo effects of FGF include, in particular organisms, modulation of various activities, e.g., limb regeneration, lens regeneration, angiogenic effects on both normal and tumor cells, wound healing, adipocyte differentiation, and growth of various neural and myoblast cells. FGFs also exhibit potent angiogenic activities. It is thought that the angiogenic activity of FGFs is due in large part to the chemotactic and mitogenic effects of these factors on endothelial cells. In addition, constitutive expression of FGFs has been shown to induce cellular transformation in transfected cells, indicating that autocrine or paracrine stimulation by FGFs may be involved in tumor formation. These diverse cellular and physiological effects foreshadow the central importance of these receptor-ligand interactions.

The compositions and cells comprising them can be used for diagnostic purposes and to study and treat diseases associated with FGF receptors. Cells expressing cloning vehicles containing defined sequences can be used to define specific sites of an FGF receptor necessary for effecting a particular activity. Alternatively, these cells may be useful to assess the ability of a selected receptor to bind different ligands (FGFs and analogues) thereby providing a powerful tool for evaluating the potential of drugs for promoting or inhibiting specific FGF-induced cellular responses.

Cells transfected, injected, infected or electroporated with DNA or MRNA containing a full length natural FGF-R sequence will often express the native or wild type receptor and respond accordingly. Specific concentrations of a purified receptor or a receptor polypeptide fragment can be used to block the binding of the ligand (FGF) to native FGF receptors. Alternatively, antibodies to the receptor or fragment can have the same effect.

Homogeneous and defined polypeptides and DNA sequences will find use in raising antibodies. In particular, antibodies against specific regions of the receptor, e.g., the ligand-binding domain, will find use in diagnostic testing. The reagents FGF-R, FGF-R polypeptides and antibodies to specific regions of the receptor can be used to study regulation of FGF mediated activities. For example, FGF agonists should stimulate blood vessel development, an effect particularly beneficial in wound healing and in the growth of collateral blood vessels in ischemic areas of the heart. FGF antagonists should find use in preventing aberrant angiogenesis as seen in diabetic retinopathy and rheumatoid arthritis or in controlling tumors by blocking proliferation of vascularization to a tumor.

II. Polypeptides

This invention includes fibroblast growth factor receptor polypeptides and proteins having FGF-R ligand-binding activity. The receptors of the present invention include FGF receptor amino acid sequences such as the amino acid sequences for a chicken bFGF-R and human FGF-R forms as shown in FIGS. 3, 4, and 7. Also included are homologous sequences, allelic variations, natural mutants, induced mutants, alternatively expressed variants, and proteins encoded by DNA which hybridize under high or low stringency conditions, to FGF receptor encoding nucleic acids retrieved from naturally occurring material. Closely related FGF-receptors retrieved by antisera to FGF receptors are also included.

The symbols for the amino acid residues are shown in Table I.

TABLE I

Abbreviations for the Amino Acid Residues

| A, Ala; | G, Gly; | M, Met; | S, Ser; |
|---|---|---|---|
| C, Cys; | H, His; | N, Asn; | T, Thr; |
| D, Asp; | I, Ile; | P, Pro; | V, Val; |
| E, Glu; | K, Lys; | Q, Gln; | W, Trp; |
| F, Phe; | L, Leu; | R, Arg; | Y, Tyr; |

X, any amino acid and Z, termination.

Various new human FGF receptors have been cloned and characterized, as described further below. Of particular note, various shorter forms (h2 and h3) and soluble versions (h4 and h5) of FGF receptors have been discovered. The soluble proteins (e.g., forms lacking a transmembrane segment) which possess FGF binding capacity indicates that shorter forms will find therapeutic and/or diagnostic uses.

Typically, the fibroblast growth factor receptor peptides of the present invention will exhibit at least about 85% homology with the naturally-occurring receptors in the IgII and IgIII regions, usually at least about 90% homology, and preferably at least about 95% homology.

In particular, the ligand binding function is localized to the extracellular domain, and the soluble forms retain this particular function. Soluble fragments of FGF receptors should be useful in substituting for or interfering with the functions of the naturally soluble variants. Alternatively, the soluble forms may interfere with dimerization of FGF receptors, since the receptors may normally be in a dimer form. Receptor dimerization may be essential for proper physiological signal transduction.

The human receptors possessing a transmembrane segment are unusual in having only the IgII and IgIII of the three Ig domains. The absence of the IgI domain indicates that certain functions may be absent in the human receptor, or, more likely, that the IgI domain is unnecessary in the human receptor. Data presented below shows that the IgI domain is not essential for ligand binding.

As used herein, the terms substantially pure and homogenous describe a protein which has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially pure protein will typically comprise over about 85 to 90% of a protein sample, more usually will comprise at least about 95%, and preferably will be over about 99% pure. Normally, purity is measured on a polyacrylamide gel, with homogeneity determined by staining. For certain purposes high resolution will be used and HPLC or a similar means for purification utilized. For most purposes, a simple chromatography column or polyacrylamide gel will be used to determine purity.

A protein is substantially free of naturally-associated components when it is separated from the native contaminants which accompany it in its natural state. Thus, a protein which is chemically synthesized or synthesized in a cellular system different from the cell from which it naturally originates will be substantially free from its naturally-associated components. The term is used to describe receptors and nucleic acids which have been synthesized in heterologous mammalian cells or plant cells, E. coli and other prokaryotes.

A polypeptide is substantially an entire membrane bound form of an FGF-R when it is substantially a full length peptide corresponding to, or highly homologous to a naturally occurring membrane bound form of an FGF-R.

Whether soluble or membrane bound, the present invention provides for substantially pure preparations. Various methods for their isolation from biological material may be devised, based in part upon the structural and functional descriptions contained herein.

FGF receptor peptides including chicken and human FGF receptors may be purified using techniques of classical protein chemistry, see below. For example, a lectin affinity chromatography step may be used, followed by a highly specific ligand affinity chromatography procedure that utilizes an FGF conjugated to biotin through the cysteine residues of the FGF. Purified FGF-R receptors may also be obtained by a method such as FGF affinity chromatography using activated CH-Sepharose coupled to FGF through primary amino groups as described in Imamura, suDra. This method, however, while resulting in a purified protein, may not provide a workable amount of purified protein (i.e. more than nanogram amounts).

Depending on the availability of specific antibodies, as provided herein, specific FGF receptors may also be purified using immunoaffinity chromatography. Antibodies prepared, as described below, may be immobilized to an inert substance to generate a highly specific affinity column. See Harlow and Lane, below.

By way of example and not limitation, one purification procedure may be used which takes advantage of the fact that labeled biotin-bFGF binds with high affinity to receptors in cells containing high amounts of those receptors. $^{125}$I-labeled biotin-bFGF will bind to bFGF receptors in Swiss 3T3 cells and can be cross-linked to the receptor protein.

Various cell or tissue sources may be selected as starting materials usually selected due to an abundance of the desired receptor. Chicken embryos (day 6, stage 29–30) are preferred because they contain relatively large amounts of the receptor protein as determined by high-affinity binding of human and bovine bFGF. Embryo extracts can first be fractionated on wheat germ agglutinin (WGA) Sepharose 4B and the partially purified bFGF receptors then bound to biotin-bFGF. The receptor-ligand complex may be adsorbed to an avidin-agarose due to the high affinity interaction between the biotin and avidin moieties. The avidin-agarose columns may be eluted with compounds which dissociate the FGF from its receptor such as suramin or SDS. The chicken protein which bound to avidin-agarose in an FGF-dependent manner migrated at the expected size (130 kDa) of the bFGF receptor. See FIG. 2B.

To determine the amino acid sequence or to obtain polypeptide fragments of the receptor, the receptor may be digested with trypsin. Peptide fragments may be separated by reversed-phase high performance liquid chromatography (HPLC) and analyzed by gas-phase sequencing. Other sequencing methods known in the art may also be used.

The FGF receptors or the specific external regions of the receptors may be used to affinity purify respective FGFS. The external region comprising the ligand-binding domain of the chicken bFGF-R shown in FIG. 3 extends from about amino acid 22 to about amino acid 374. The ligand-binding domain of the human FGF-R shown in FIG. 4 extends from about amino acid 22 to about amino acid 285. The ligand-binding domain varies with different FGF receptors and may be anywhere from 5% to 100% of the extracellular region. The minimal amount of protein sequence necessary for ligand bonding may be determined by excising various segments of the extracellular domain and assaying ligand binding to the remaining sequence. Studies of ligand-receptor interaction indicate that at least the ligand-binding region is located in the extracellular region of the receptor is required. As used in this application, FGF receptor or FGF-R ligand-binding activity means having the ability to bind a fibroblast growth factor or other specific ligand. Usually these ligands will be members of the FGF family. Therefore the external region has utility in establishing FGF agonists or antagonists.

It is also likely that the FGF-R, like many other growth factor receptors, is found naturally in a multimeric protein complex, most likely in dimer form. Thus, other important regions of a receptor will be those, either extracellular or otherwise, which are involved in dimerization.

The intracellular regions of the receptors (e.g. starting at about amino acid 396 through the COOH-terminus for the chicken bFGF-R and about amino acid 307 through the COOH-terminus for the human FGF-R shown in FIGS. 3 and 4, respectively) may also be used as enzymes with tyrosine kinase activity. The bek gene has 84% amino acid sequence identity to the analogous region (tyrosine kinase region) of the chicken bFGF-R. The flg has 99% homology with various sequences of the human FGF receptor described in FIG. 4.

A signal or leader sequence directs a protein through the membrane of a cell. The signal sequences of the receptors may be used in conjunction with their respective receptors but may also be used with other proteins (e.g. amino acids about 1 through 21 of the N-terminal sequence comprise the leader or signal sequence of the chicken bFGF-R shown in FIG. 3 and the human FGF-R shown in FIG. 4).

The present invention also provides for analogues of the fibroblast growth factor receptor polypeptides. Such analogues include both modifications to a polypeptide backbone and variants and mutants of the polypeptides. Modifications include chemical derivatizations of polypeptides, such as acetylations, carboxylations and the like. They also include glycosylation modifications and processing variants of a typical polypeptide. These processing steps specifically include enzymatic modifications, such as ubiquinization. See, e.g., Hershko and Ciechanover (1982), "Mechanisms of Intracellular Protein Breakdown," *Ann. Rev. Bioch.*, 51:335–364.

Other analogues include genetic variants, both natural and induced. Induced mutants may be derived from various techniques including both random mutagenesis of the encoding nucleic acids using irradiation or exposure to EMS, or may take the form of engineered changes by site-specific mutagenesis or other techniques of modern molecular biology. See, Sambrook, Fritsch and Maniatis (1989), *Molecular Cloning: A Laboratory Manual* (2d ed.), CSH Press.

Besides substantially full-length polypeptides, the present invention provides for biologically active fragments of the polypeptides. Significant biological activities include ligand-binding, immunological activity and other biological activities characteristic of fibroblast growth factor receptor polypeptides. Immunological activities include both immunogenic function in a target immune system, as well as sharing of immunological epitopes for binding, serving as either a competitor or substitute antigen for a fibroblast growth factor receptor epitope. As used herein, the term segment, as applied to a polypeptide, will ordinarily be at least about 5 contiguous amino acids, typically at least about 7 contiguous amino acids, more typically at least about 9 contiguous amino acids, usually at least about 11 contiguous amino acids, preferably at least about 13 contiguous amino acids, more preferably at least about 16 contiguous amino acids, and most preferably at least about 20 to 30 or more contiguous amino acids. Segments of a particular domain will be segments of the appropriate size within the corresponding domain.

For example, ligand-binding or other domains may be "swapped" between different new fusion polypeptides or fragments. Thus, new chimeric polypeptides exhibiting new combinations of specificities result from the functional linkage of ligand-binding specificities and intracellular domains. For example, the Ig domains may be substituted by Ig domains from other related polypeptides.

For immunological purposes, immunogens may be produced which tandemly repeat polypeptide segments, thereby producing highly antigenic proteins. Alternatively, such polypeptides will serve as highly efficient competitors for specific binding. Production of antibodies to fibroblast growth factor receptor polypeptides is described below.

The present invention also provides for other polypeptides comprising fragments of fibroblast growth factor receptors. Thus, fusion polypeptides between the receptors and other homologous or heterologous proteins are provided. Homologous polypeptides may be fusions between different growth factor receptors, resulting in, for instance, a hybrid protein exhibiting ligand specificity of one receptor and the intracellular domain of another, or a receptor which may have broadened or weakened specificity of binding. Likewise, heterologous fusions may be constructed which would exhibit a combination of properties or activities of the derivative proteins. Typical examples are fusions of a reporter polypeptide, e.g., luciferase, with a domain of a receptor, e.g., a ligand-binding domain, so that the presence or location of a desired ligand may be easily determined. See, e.g., Dull et al., U.S. Pat. No. 4,859,609, which is hereby incorporated herein by reference. Other gene fusion partners include bacterial β-galactosidase, trpE Protein A, β-lactamase, alpha amylase, alcohol dehydrogenase and yeast alpha mating factor. See, e.g., Godowski et al. (1988), *Science* 241:812–816; and Experimental section below.

Fusion proteins will typically be made by either recombinant nucleic acid methods or by synthetic polypeptide methods. Techniques for nucleic acid manipulation are described generally, for example, in Sambrook et al. (1989), *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield, *J. Amer. Chem. Soc.* 85:2149–2156 (1963). The recombinant nucleic acid sequences used to produce fusion proteins of the present invention may be derived from natural or synthetic sequences. Many natural gene sequences are obtainable from various cDNA or from genomic libraries using appropriate probes. See, GenBank™, National Institutes of Health. Typical probes for fibroblast growth factor receptors may be selected from the sequences of FIGS. 3, 4, or 9 in accordance with standard procedures. Suitable synthetic DNA fragments may be prepared by the phosphoramidite method described by Beaucage and Carruthers, *Tetra. Letts.* 22:1859–1862 (1981). A double stranded fragment may then be obtained either by synthesizing the complementary strand and annealing the strand together under appropriate conditions or by adding the complementary strand using DNA polymerase with an appropriate primer sequence.

III. NUCLEIC ACIDS

The present invention provides nucleic acid sequences encoding various FGF receptor sequences described above. FIGS. 3, 4, and 7 respectively set forth the corresponding cDNA sequences encoding chicken and human FGF receptors.

In FIG. 3 showing the chicken bFGF-R, peptides sequenced from purified protein are underlined, including the NH$_2$-proximal sequences from amino acids 35–3 (ala - - - arg), 56–67 (leu - - - arg), and 139-158 (glu - - - lys). The transmembrane sequence is indicated by a dark bar, a unique acidic amino acid region is outlined, cysteine residues are circled, potential N-linked glycosylation sites are indicated by a dot and the dashed underlining indicates the putative hydrophobic signal sequence. The amino acid sequence includes an in-frame stop codon (about residue –12) followed by an initiator methionine. The structural sequence begins at about amino acid 22.

In FIG. 4 showing the human FGF-R, the methionine of codon ATG starting at about nucleotide 529 is the first amino acid of the FGF-R gene. For example, amino acid 22 of the receptor described in FIG. 4 is an arginine residue (R) located two amino acids in from the left, two lines up from the bottom between "589" and "630" on page 1 of FIG. 4.

Nucleic acids according to the present invention will possess a sequence which is either derived from a natural human, chicken, or other FGF-R gene or one having substantial homology with a natural FGF-R gene or a portion thereof.

Substantial homology in the nucleic acid context means either that the segments, or their complementary strands, when optimally aligned and compared, are identical with appropriate nucleotide insertions or deletions, in at least about 80% of the residues, usually at least about 90%, more usually at least about 95%, preferably at least about 97%, and more preferably at least about 98 to 99.5% of the nucleotides. Alternatively, substantial homology exists when the segments will hybridize under selective hybridization conditions, to a strand, or its complement, typically using a sequence derived from FIGS. 3, 4, or 9. Selectivity of hybridization exists when hybridization occurs which is more selective than total lack of specificity. Typically, selective hybridization will occur when there is at least about 55% homology over a stretch of at least about 14/25 nucleotides, preferably at least about 65%, more preferably at least about 75%, and most preferably at least about 90%. See, Kanehisa, M. (1984), *Nucleic Acids Res.* 12:203–213, which is incorporated herein by reference. Stringent hybridization conditions will typically include salt concentrations of less than about 1 M, more usually less than about 500 mM and preferably less than about 200 mM. Temperature conditions will typically be greater than 20° C., more usually greater than about 30° C. and preferably in excess of about 37° C. As other factors may significantly affect the stringency of hybridization, including, among others, base composition and size of the complementary strands, presence of organic solvents and extent of base mismatching, the combination of parameters is more important than the absolute measure of any one.

An isolated nucleic acid is one which has been substantially purified away from other sequences which normally accompany it, e.g., other cellular nucleic acid sequences. Usually, the term refers to a fragment of a genome which has been selectively cloned, isolated and purified to substantial homogeneity.

Probes may be prepared based on the sequence of the FGF receptor cDNAs provided in FIGS. 3, 4, and 9. The probes will include an isolated nucleic acid attached to a label or reporter molecule and may be used to isolate other FGF receptor nucleic acid sequences by standard methods. See, e.g. J. Sambrook et al., *Molecular Cloning: A Laboratory Manual*, vols. 1–3, CSH Press, N.Y. (1989), which is hereby incorporated herein by reference. Other similar nucleic acids may be selected for by using homologous nucleic acids. Alternatively, nucleic acids encoding these same or similar receptor polypeptides may be synthesized or selected by making use of the redundancy in the genetic code. Various codon substitutions may be introduced, e.g., silent changes thereby producing various restriction sites, or to optimize expression for a particular system. Mutations may be introduced to modify the properties of the receptors, perhaps to change the ligand binding affinities, the inter-chain affinities, or the polypeptide degradation or turnover rate.

The DNA compositions of this invention may be derived from genomic DNA or cDNA, prepared by synthesis or may be a hybrid of the various combinations. Recombinant nucleic acids comprising sequences otherwise not naturally occurring are also provided by this invention. An isolated DNA sequence includes any sequence that has been obtained by primer or hybridization reactions or subjected to treatment with restriction enzymes or the like.

Synthetic oligonucleotides can be formulated by the triester method according to Matteucci, et al., *J. Am. Chem. Soc.*, 103:3185 (1981) or by other methods such as commercial automated oligonucleotide synthesizers. Oligonucleotides can be labeled by excess polynucleotide kinase (e.g., about 10 units to 0.1 nmole substrate is used in connection with 50 mM Tris, pH 7.6, 5 mM dithiothreitol, 10 mM $MgCl_2$, 1–2 mM ATP, 1.7 pmoles $^{32}$P-ATP (2.9 mCi/mmole) 0.1 mM spermidine, 0.1 mM EDTA). Probes may also be prepared by nick translation, Klenow fill-in reaction, or other methods known in the art.

cDNA or genomic libraries of various types may be screened. The choice of cDNA libraries normally corresponds to a tissue source which is abundant in mRNA for the desired receptors. Phage libraries are normally preferred, but plasmid libraries may also be used. For example, a keratinocyte cell genomic or cDNA library would be preferred to isolate and clone a keratinocyte growth factor receptor. Embryonic or placental libraries can be used for int-2, FGF-5 and hst receptors and an endothelial cell library is preferred for acidic FGF receptors. Clones of a library are spread onto plates, transferred to a substrate for screening, denatured and probed for the presence of desired sequences.

For example, with a plaque hybridization procedure, each plate containing bacteriophage plaques is replicated onto duplicate nitrocellulose filter papers (Millipore-HATF). The phage DNA is denatured with a buffer such as 500 mM NaOH, 1.5 M NaCl for about 1 minute, and neutralized with, e.g., 0.5 M Tris-HCl, pH 7.5, 1.5 M NaCl (3 times for 10 minutes each). The filters are then washed. After drying, the filters are typically baked, e.g., for 2 hours at 80° C. in a vacuum oven. The duplicate filters are prehybridized at 42° C. for 4–24 hours with 10 ml per filter of DNA hybridization buffer (20–50% formamide, 5×SSC, pH 7.0, 5×Denhardt's solution (polyvinylpyrrolidone, plus Ficoll and bovine serum albumin; 1X=0.02% of each), 50 mM sodium phosphate buffer at pH 7.0, 0.2% SDS, and 50 µg/ml denatured salmon sperm DNA). Hybridization with an appropriate probe may be performed at 42° C. for 16 hrs with 10 ml/filter of 1×10$^6$ cpm/ml of DNA hybridization buffer containing labeled probe. The final concentration of formamide is varied according to the length of the probe and the degree of stringency desired. See, e.g., J. G. Wetmur ad Davidson, *J. Mol. Biol.* 31:349–370 (1968); and M. Kanehisa, *Nuc. Acids Res.* 12:203–213 (1984), each of which is incorporated herein by reference, for a discussion of hybridization conditions and sequence homology.

An oligonucleotide probe based on the amino acid sequence of the two tryptic peptides of the purified chicken bFGF-R was used to screen a chicken embryo (day 6) cDNA library under low stringency conditions. Sequences corresponding to TVALGSNVEFVCK and VYSDPQPHIQWLY, prepared using a commercial automated oligonucleotide synthesizer (Applied Biosystems) were used to obtain the chicken bFGF receptor clone described in FIG. 3. This clone, or sequences derived from it, can be used to isolate bFGF-Rs in other species as well as other FGF-Rs in a target species.

The probes described above which were used to isolate the chicken bFGF-R were also used to isolate a human bFGF receptor CDNA clone.

In accordance with this invention any isolated DNA sequence which encodes an FGF-R complete structural sequence can be used as a probe. Alternatively, any DNA sequence that encodes an FGF-R hydrophobic signal sequence and its translational start site may be used. Any isolated partial DNA sequence which encodes an FGF-R activity (e.g. ligand-binding or FGF-R binding) is also part of this invention. Preferred probes are cDNA clones of each isolated FGF receptor.

The DNA sequences used in this invention will usually comprise at least about 5 codons (15 nucleotides), more usually at least about 7 codons, typically at least about 10 codons, preferably at least about 15 codons, more preferably at least about 25 codons and most preferably at least about 35 codons. One or more introns may also be present. This number of nucleotides is usually about the minimal lenath required for a successful probe that would hybridize specifically with an FGF receptor. For example, epitopes characteristic of an FGF-R may be encoded in short peptides. Usually the wild-type sequence will be employed, in some instances one or more mutations may be introduced, such as deletions, substitutions, insertions or inversions resulting in changes in the amino acid sequence to provide silent mutations, to modify a restriction site, or to provide specific mutations. The genomic sequence will usually not exceed about 200 kb, more usually not exceed about 100 kb, preferably not be greater than 0.5 kb.

Portions of the DNA sequence having at least about 15 nucleotides, usually at least about 15 nucleotides, and fewer than about 6 kd, usually fewer than about 1.0 kb, from a DNA sequence encoding an FGF receptor are preferred as probes. The probes may also be used to determine whether mRNA encoding a specific FGF-R is present in a cell or different tissues.

The natural or synthetic DNA fragments coding for a desired fibroblast growth factor receptor fragment will be incorporated into DNA constructs capable of introduction to and expression in an in vitro cell culture. Usually the DNA constructs will be suitable for replication in a unicellular host, such as yeast or bacteria, but may also be intended for introduction to, with and without and integration within the genome, cultured mammalian or plant or other eukaryotic cell lines. DNA constructs prepared for introduction into bacteria or yeast will typically include a replication system recognized by the host, the intended DNA fragment encoding the desired receptor polypeptide, transcription and translational initiation regulatory sequences operably linked to the polypeptide encoding segment and transcriptional and translational termination regulatory sequences operably linked to the polypeptide encoding segment. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known. See, Sambrook et al. (1989). Conveniently available expression vectors which include the replication system and transcriptional and translational regulatory sequences together with the insertion site for the fibroblast growth factor receptor DNA sequence may be employed. Examples of workable combinations of cell lines and expression vectors are described in Sambrook et al. (1989); see also, Metzger et al. (1988), *Nature* 334:31–36.

Expression vectors for these cells can include expression control sequences, such as an origin of replication, a promoter, an enhancer and necessary processing information sites, such as ribosome-binding sites, RNA splice sites, polyadenylation sites, and transcriptional terminator sequences. Preferably, the enhancers or promoters will be those naturally associated with genes encoding the fibroblast growth factor receptors, although it will be understood that in many cases others will be equally or more appropriate.

Other preferred expression control sequences are enhancers or promoters derived from viruses, such as SV40, Adenovirus, Bovine Papilloma Virus, and the like.

Similarly, preferred promoters are those found naturally in immunoglobulin-producing cells (see, U.S. Pat. No. 4,663,281, which is incorporated herein by reference), but SV40, polyoma virus, cytomegalovirus (human or murine) and the LTR from various retroviruses (such as murine leukemia virus, murine or Rous sarcoma virus and HIV) may be utilized, as well sa promoters endogenous to FGF-R genes. See, *Enhancers and Eukarvotic Gene Expression*, Cold Spring Harbor Press, N.Y., 1983, which is incorporated herein by reference.

The vectors containing the DNA segments of interest (e.g., a fibroblast growth factor receptor gene or cDNA sequence or portions thereof) can be transferred into the host cell by well-known methods, which vary depending on the type of cellular host. For example, calcium chloride transfection is commonly utilized for procaryotic cells, whereas calcium phosphate treatment may be used for other cellular hosts. See generally, Sambrook et al. (1989), *Molecular Cloning: A Laboratory Manual* (2d ed.), CSH Press (1989), which is incorporated herein by reference. The term "transformed cell" is meant to also include the progeny of a transformed cell.

As with the purified polypeptides, the nucleic acid segments associated with the ligand-binding segment, the extracellular domain and the intracellular domain are particularly useful. These gene segments will be used as probes for screening for new genes exhibiting similar biological activities, though the controlling elements of these genes may also be of importance.

IV. METHODS FOR MAKING FGF RECEPTORS

DNA sequences may also be used to express polypeptides which exhibit or inhibit FGF receptor activity. For example, a DNA sequence of from about 21 nucleotides (about 7 amino acids) to about 2.1 kb (about 700 amino acids) may be used to express a polypeptide having an FGF receptor specific activity, typically ligand-binding.

Large quantities of the receptor proteins may be prepared by expressing the whole receptor or parts of the receptor contained in the expression vehicles in compatible hosts such as *E. coli*, yeast, mammalian cells, insect cells or frog oocytes. The expression vehicles may be introduced into the cells using methods well known in the art such as calcium phosphate precipitation (discussed below), lipofection, electroporation or DEAE dextran.

Usually the mammalian cell hosts will be immortalized cell lines. To study the characteristics of an FGF-R and its corresponding growth factor, it will be useful to transfect, etc. mammalian cells which lack or have low levels of an FGF receptor where the signal sequence directs the peptide into the cell membrane. Cells without significant FGF receptors include lymphocytes, myocytes, green monkey cos-7 cells and Chinese hamster ovary cells (CHO). Transformed or transfected, etc., cells encode a receptor that is functionally equivalent to a wild-type receptor and confers a FGF-sensitive mitogenic response on the cell. Such cells will enable one to analyze the binding properties of various native FGFs. Transfected cells may also be used to evaluate a composition or drug's effectiveness as an FGF antagonist or agonist. The level of receptor tyrosine kinase activity or the rate of nucleic acid synthesis can be determined by contacting transfected cells with drugs and comparing the effects of FGFs or their analogs on the drug-treated cells versus the controls. Although the most common prokaryote cells used as hosts are strains of *E. coli*, other prokaryotes such as *Bacillus subtilis* or Pseudomonas may also be used. The DNA sequence of the invention, including fragments or portions of the sequence encoding for an entire receptor, a portion of the receptor or a polypeptide having an FGF-R activity can be used to prepare an expression vehicle or construct for an FGF-R or polypeptide having an FGF-R activity. Usually the control sequence will be a eukaryotic promoter for expression in a mammalian cell. In some vehicles, the receptor's own control sequences may also be used. A common procaryotic plasmid vector for transforming *E. coli* is pBR322 or its derivatives (e.g. the plasmid pkt279 (Clontech)) (Bolavar et al., *Gene*, 2:95 (1977)). The procaryotic vectors may also contain procaryotic promoters for transcription initiation, optionally with an operator. Examples of most commonly used procaryotic promoters include the beta-lactamase (penicillinase) and lactose (lac) promoter (Cheng et al., *Nature*, 198:1056 (1977), the tryptophan promoter (trp) (Goeddell et al., *Nucleic Acid Res.*, 8: 457 (1980)) the $P_L$ promoter and the N-gene ribosome binding site (Shimatake et al., *Nature*, 292:128 (1981).

Promoters used in conjunction with yeast can be promoters derived from the enolase gene (Holland et al., *J Biol. Chem.*, 256:1385 (1981)) or the promoter for the synthesis of glycolytic enzymes such as 3-phosphoglycerate kinase (Hitzeman et al., *J. Biol. Chem.*, 255 (1980)).

Appropriate non-native mammalian promoters might include the early and late promoters from SV40 (Fiers et al., *Nature*, 273:113 (1978) or promoters derived from murine molony leukemia virus, mouse mammary tumor virus, avian sarcoma viruses, adenovirus II, bovine papilloma virus or polyoma. In addition, the construct may be joined to an amplifiable gene (e.g. DHFR) so that multiple copies of the FGF receptor gene may be made.

Prokaryotes may be transformed by various methods, including using $CaCl_2$ (Cohen, S. N., *Proc. Natl. Acad. Sci. USA*, 69:2110 (1972)) or the RbCl method (Maniatis et al., *Molecular Cloning: A Laboratory Manual*, Cold Spring Harbor Press 1982)). Yeast may be transformed using a method described by Van Solingen et al.,*J. Bacter.*, 130:946 (1977) and C. L. Hsiao et al., *Proc. Natl. Acad. Sci. USA*, 76:3829 (1979). With respect to eukaryotes, mammalian cells may be transfected using a calcium phosphate precipitation method described by (Graham and van der Eb, *Virology*, 52:546 (1978)), or by lipofectin (BRL) or retroviral infection (E. Gilboa, *Experimental Manipulation of Gene Expression*, Chap. 9, Academic Press P. 175 (1983)). The actual expression vectors containing appropriate sequences may be prepared according to standard techniques involving ligation and restriction enzymes (See e.g., Maniatis supra.) Commercially available restriction enzymes for cleaving specific sites of DNA may be obtained from New England BioLabs, Waltham, Mass.

Clones are selected by using markers depending on the mode of the vector construction. The marker may be on the same or a different DNA molecule preferably the same DNA molecule. With mammalian cells the receptor gene itself may be the best marker. In procaryotic hosts the transformant may be selected by resistance to ampicillin, tetracycline or other antibiotics. Production of a particular product based on temperature sensitivity may also serve as an appropriate marker. Various methods may be used to harvest and purify the FGF-R receptor protein or peptide fragment. The peptide may be isolated from a lysate of the host. The peptide may be isolated from the cell supernatant if the peptide is secreted. The FGF-R peptide is then further purified as discussed above using HPLC, electrophoresis, affinity chromatography (preferably immuno-affinity or ligand affinity).

Another method which can be used to isolate cDNA clones of FGF-R related species involves the use of the polymerase chain reaction (PCR). (Saiki, R. K., et al. *Science* 230: 1350 (1985). In this approach two oligonucleorides (27mers) corresponding to distinct regions of the FGF-R sequence are synthesized and then used in the PCR reaction to amplify receptor-related mRNA transcripts from an mRNA source. Annealing of the oligonucleotides and PCR reaction condition are performed under conditions of reduced stringency as described below in Example 2. The resulting amplified fragments are subcloned, and the resulting recombinant colonies are probed with $^{32}$P-labeled full-length FGF-R CDNA using both high and low stringency conditions (see Examples 2 and 3). Clones which hybridize under low but not high stringency conditions represent FGF-R related mRNA transcripts. In addition this approach can be used to isolate variant FGF-R cDNA species which arise as a result of alternative splicing, see Frohman, M. A., et al., *Proc. Natl. Acad. Sci. USA*, 85: 8998 (1988).

V. ANTIBODIES

Polyclonal and/or monoclonal antibodies to the various FGF receptors and peptide fragments may also be prepared. The term antibody is used both to refer to a homogeneous molecular entity, or a mixture such as a serum product made up of a plurality of different molecular entities. Peptide fragments may be prepared synthetically in a peptide synthesizer and coupled to a carrier molecule (i.e. keyhole limpet hemocyanin) and injected into rabbits over several months. The rabbit sera is tested for immunoreactivity to the FGF receptor protein or fragment. Monoclonal antibodies may be made by injecting mice with FGF-R protein, FGF-R polypeptides or mouse cells expressing high levels of the cloned FGF receptor on its cell surface. Monoclonal antibodies will be screened by ELISA and tested for specific immunoreactivity with the FGF receptor protein or polypeptides thereof. See, E. Harlow and D. Lane, *Antibodies: A Laboratory Manual*, CSH Laboratories (1988), which is hereby incorporated herein by reference. These antibodies will be useful in assays as well as pharmaceuticals.

Once a sufficient quantity of the desired fibroblast growth factor receptor polypeptide has been obtained, the protein may be used for various purposes. A typical use is the production of antibodies specific for binding to these receptors. These antibodies may be either polyclonal or monoclonal and may be produced by in vitro or in vivo techniques.

For production of polyclonal antibodies, an appropriate target immune system is selected, typically a mouse or rabbit. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species may be substituted for a mouse or rabbit.

An immunological response is usually assayed with an immunoassay. Normally such immunoassays involve some purification of a source of antigen, for example, produced by the same cells and in the same fashion as the antigen was produced. The immunoassay may be a radioimmunoassay, an enzyme-linked assay (ELISA), a fluorescent assay, or any of many other choices, most of which are functionally equivalent but may exhibit advantages under specific conditions.

Monoclonal antibodies with affinities of $10^8$ M$^{-1}$ preferably $10^9$ to $10^{10}$, or stronger will typically be made by standard procedures as described, e.g., in Harlow and Lane, *Antibodies: A Laboratory Manual*, CSH Laboratory (1988); or Goding, *Monoclonal Antibodies: Principles and Practice* (2d ed) Academic Press, New York (1986), which are hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al., "Generation of a Large Combinatorial Library of the Immunoglobulin Repertoire in Phage Lambda," *Science* 246:1275–1281 (1989), hereby incorporated herein by reference. The polypeptides and antibodies of the present invention may be used with or without modification. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

VIII. METHODS FOR USE

The present invention provides a fibroblast growth factor-receptor (FGF-R) purification method as well as a method for synthesizing FGF receptors within cells. Also provided are the homogeneous receptors produced by these methods, the nucleic acid sequences encoding the receptors or portions of the receptors, as well as the expression vehicles containing these sequences, cells comprising the FGF-receptors and antibodies to the receptors. Of particular interest are the soluble forms of the receptors, which have binding sites which may compete with receptors to bind FGF.

However, as indicated above, the FGF-R likely functions in a dimer state. The soluble forms of the receptor may interfere with the dimerization and may be effective in blocking signal transduction by a different mechanism from competitive affinity for the FGF ligands. The soluble, or intracellular or transmembrane fragments of the various receptor forms are expected to interfere with dimer formation and thus can serve to block at least some types of, or some fraction of signal transduction.

This observation provides a method for modifying in vivo a fibroblast growth factor receptor modulated activity comprising administering to a patient an amount of a fibroblast growth factor receptor blocking agent effective to inhibit fibroblast growth factor binding to fibroblast growth factor receptors. As discussed above, the FGF family of proteins have a significant role in regulating many important physiological processes. The soluble FGF-R polypeptides may be effective in modifying the extent of FGF modulation of these processes. For this reason, the soluble forms of the receptors may find use as competitive binding sites for FGF. Likewise, truncated FGF binding sites or binding sites which have been mutated, particularly those from the human forms described, may be equally effective in this effect at a lesser cost, both in terms of economics and in terms of medical side-effects upon administration.

The reagents provided herein will also find use in diagnosis of either FGF production or FGF-R production. Various medical conditions are indicated by an abnormal level of production of either of these proteins, including, e.g., Kaposi sarcoma, which produces Kaposi FGF, and diabetic retinopathy. Thus, diagnostic tests dependent upon these reagents now become available.

With the different FGF types, there is a likelihood that different types of receptors exist having variations in affinities for the various ligands. With the genes and proteins of the present invention, distinctions between various receptor types will be found. Thus, tissue markers should become available.

Since tumor growth is so dependent upon microvascularization, administration of the FGF-R may serve to prevent such and result in suppression of tumor growth. By prevention of the FGF activation, the present invention may be an important addition to the arsenal of agents for fighting tumor growth.

Viral infections may also be dependent upon binding to particular receptors for the invasion process. There is suggestive evidence that HSV (Herpes simplex virus) infects by binding to FGF-R proteins. Thus, administration of therapeutically effective amounts of FGF-R soluble forms or fragments may serve as a prophylactic measure to minimize the risk of exposure to this, or other viruses, making use of this mechanism for cell entry. Again, the mechanism of protection may depend upon competitive binding, disruption of dimer structure, a combination, or another.

The quantities of reagents necessary for effective therapy will depend upon many different factors, including means of administration, target site, physiological state of the patient, and other medicants administered. Thus, one should titrate the dosage for treatment of particular conditions. Typically, dosages used in vitro may provide useful guidance in the amounts useful for in situ administration of these reagents. Animal testing of dosages for treatment of particular disorders will provide further predictive indication of human dosage. Various considerations are described in Gilman et al., *Goodman and Gilman's: The Pharmacological Basis of Therapeutics*, 7th Ed., MacMillan, New York (1985), which is hereby incorporated herein by reference. Because of the high affinity binding between FGF and its receptors, low dosages of these reagents would be initially expected to be effective. Thus, dosage ranges would ordinarily be expected to be in amounts lower than mM concentrations, typically less than about 10 μM concentrations, usually less than about 100 nM concentrations, more usually less than about 1 nM, preferably less than about 10 pM (picomolar), more preferably less than about 100 fM (femtomolar), and most preferably less than about 1 fM, with an appropriate carrier.

The invention will better be understood by reference to the following illustrative examples.

EXAMPLE 1

Characterization of a bFGF Receptor $^{125}$I-labeled bFGF was first competitively bound to Swiss 3T3 cells. As shown in FIG. 1(A), $^{125}$I-labeled bFGF (2 Ci/μmol) was added to the confluent 3T3 cells (6 fmol of $^{125}$I-labeled bFGF per $10^5$ cells) in the presence of indicated concentrations of: unmodified bFGF (-X-); biotin-bFGF (solid square); the unbound fraction after biotin-bFGF was incubated with avidin-agarose, (open square); the unbound fraction after bFGF was incubated with avidin-agarose, (open triangle). Binding was performed for 30 min at 37° C. in culture media (DME H21) containing 0.2% gelatin, and heparin (15 U/ml). The cells were washed three times with a buffer containing 20 mM HEPES (pH 7.4), 0.2% gelatin, and 150 mM NaCl. The radioactivity present was determined in a Beckman gamma counter. Maximal binding (0% inhibition) represents 5700 cpm of specific binding (nonspecific binding was 600 cpm). All determinations were made in triplicate. Recombinant human bFGF (Barr et al., *J. Biol. Chem.*, 263: 16471 (1988)) was iodinated using IODO-BEADS (Pierce). The bFGF was iodinated using 0.5- lmCi; of $^{125}$I per 1 μg FGF, 0.2M NaPi, pH 7.4, 2 IODOBEADS and incubated for 15 min. at room temperature, quenched with Na metabisulfite and excess KI. Iodinated bFGF was separated from unreacted free iodine by gel filtration on a PD 10 column equilibrated with 0.2M Na phosphate, pH 7.5, 0.2M NaCl, 0.2% gelatin. The bFGF was biotinylated using iodoacetyl-LC-biotin (Pierce) at a 4:1 molar excess of cysteine residues in 10 mM Tris-HCl (pH 8.0) for 5 hours at 4° C., according to the method of Yamamoto, et al., *FEBS Lett.* 176:75 (1984). Unreacted biotin was removed by gel filtration with PD 10 columns as described above (Pharmacia). During the purification procedure, modified bFGF was indistinguishable from unmodified bFGF in its ability to inhibit the binding of $^{125}$I-labeled bFGF to high affinity bFGF receptors in Swiss 3T3 cells and in its ability to stimulate the phosphorylation of a 90 kD protein, known to be a substrate of bFGF-induced tyrosine kinase activity. See FIG. 1(A). The biotinylation reaction modified 90 to 95% of the bFGF molecules as measured by binding to avidin-conjugated agarose.

Figure 1B:
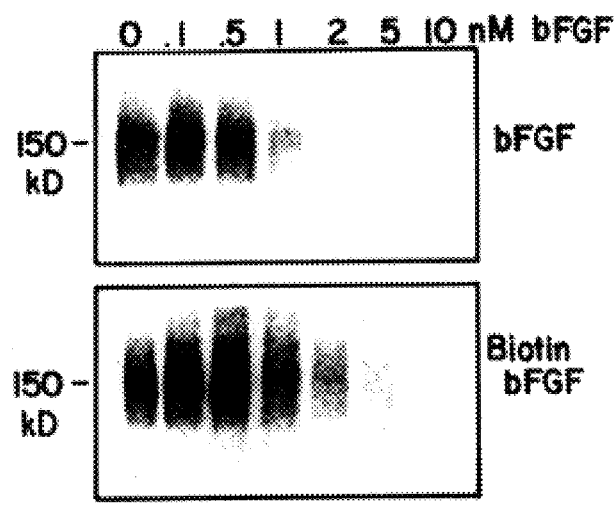
FIG. 1(B) is an autoradiograph of bFGF cross-linked Swiss 3T3 cells subjected to gel electrophoresis.

As shown in FIG. 1(B), cellular in situ bFGF receptors were cross-linked to labeled bFGF. $^{125}$I-labeled biotin-bFGF or 125I-labeled bFGF (0.1 pmol) was added to Swiss 3T3 cells ($5\times10^5$ cells) in the presence or absence of unlabeled bFGF as indicated. The cells were washed and cross-linked with 0.15 mM disuccinimidyl suberate (DSS) (Pierce). The cells were then solubilized, subjected to SDS polyacrylamide gel electrophoresis (PAGE) and $^{125}$I-labeled proteins were detected by autoradiography. $^{125}$I-labeled biotin-bFGF bound to bFGF receptors in Swiss 3T3 cells with high affinity (dissociation constant equals 1 nM) and was cross-linked to a 130 kD protein which comigrated with the bFGF receptor cross-linked to $^{125}$I-labeled bFGF.

Purified chicken bFGF receptor was prepared by homogenizing fresh day 6 chicken embryos (stage 29–30) with a Brinkmann polytron; (1500 embryos/batch); (1:1 v/v) in a final concentration of 0.25 M sucrose, 50 mM HEPES (pH 7.5), 2 mM EDTA, 50 mM NaF, 150 μM sodium orthovanadate, 30 mM sodium pyrophosphate, 1 mM phenylmethylsulfonyl fluoride (PMSF), aprotinin (20 to 30 kallikrein international units (KIU)/ml, leupeptin (10 μg/ml), and pepstatin (1 μg/ml). The homogenate was centrifuged at 17,700 g for 45 minutes at 4° C. The pellet was resuspended in homogenization buffer (300 ml) and the resulting suspension was referred to as the membrane fraction (Mb). The membrane fraction was then incubated for 30 min at 4° C. with an equal volume of 2×lysis buffer (1×lysis buffer consists of 10 mM Tris-HCl (pH 7.5)), 50 mM NaCl, 5 mM EDTA, 1% 25 Triton X-100, 50 mM NaF, 150 μM sodium orthovanadate, 30 mM sodium pyrophosphate, 1 mM PMSF, aprotinin (20 to 30 KIU/ml), leupeptin (10 µg/ml) and pepstatin (1 µg/ml)), and then centrifuged at 31,000 g for 30 min. The supernatant was applied batchwise to a 150 ml WGA-Sepharose 4B column, washed with 300 ml of lysis buffer followed by 500 ml of column buffer which contained 20 mM HEPES (pH 7.5), 2 mM EDTA, 10% glycerol, 0.1% Triton X-100, 50 mM NaF, 150 µM sodium orthovanadate, 30 mM sodium pyrophosphate, 1 mM PMSF, aprotinin (20 to 30 KIU/ml), leupeptin (10 µg/ml) and pepstatin (1 µg/ml). The column was eluted with column buffer containing 0.5 M N-acetylglucosamine. Peak protein containing fractions were combined and stored at −70° C.

To establish the presence of FGF-R in the embryo membranes and WGA eluate, chicken bFGF receptor was cross-linked by incubating 10 µl of the chicken embryo membrane fraction (Mb) or 100 µl of the eluate from the WGA-Sepharose 4B column with $^{125}$I-labeled bFGF (0.1 pmol) in the presence (+) or absence (−) of a 200-fold excess of unlabeled BFGF for 30 min at 37 C. (See FIG. 2(A)). DSS was added to a concentration of 0.15 mM, and the reaction mixture was incubated for 10 min on ice. Samples were subjected to SDS PAGE followed by autoradiography. Specific binding and cross-linking of $^{125}$I-bFGF to crude chicken embryo membrane fraction revealed only a single protein band of 150 kDa (FIG. 2(A)). After the molecular mass of bFGF was subtracted, the deduced size of the chicken bFGF receptor was 130–135 kDa.

As shown in FIG. 2(B), two large-scale ligand affinity purifications were performed (each using the material from 20,000 embryos). The eluate from the WGA-Sepharose 4B column was incubated with biotin-bFGF prepared as described above (10:1 molar excess of ligand to receptor) and heparin at a concentration of 15 U/ml (to reduce low affinity binding) for 30 min at 4° C. The mixture was then cycled twice through a 10 ml avidin-agarose column (bFGF-agarose). To determine the nonspecific binding of protein to avidin-agarose (control), the eluate from the WGA-Sepharose 4B column was cycled through avidin-agarose in the absence of biotin-bFGF (control). The columns were washed with 200 ml of column buffer used with the Sepharose column described above containing 0.2 M NaCl followed by column buffer without NaCl (300 ml) and then eluted with 10 mM suramin in column buffer. Four sequential 10 ml fractions were collected (frac. 1–4) and samples of each fraction were subjected to SDS PAGE and stained with silver nitrate. As shown in FIG. 2(B), only a single protein bound to avidin-agarose in an FGF-dependent manner and it migrated at the expected size (130 kDa) of the bFGF receptor.

The eluted proteins were separated by acrylamide gel electrophoresis and stained with Coomassie Blue. The band corresponding to the bFGF receptor was cut out and the protein electroeluted according to the method of M. W. Hunkapiller, et al., *Meth. In Enzymol.*, 91: 227 (1983). This procedure resulted in the purification of 2 to 5 ng of pure FGF receptor per chicken embryo with an overall recovery of 5%.

To further characterize the receptor, protein was digested with trypsin. Peptide fragments were isolated by reversed-phase high performance liquid chromatography (HPLC) and analyzed by gas-phase sequencing as described in Yarden et al., supra. From the two independent preparations, the amino acid sequences of 14 peptides, as shown in FIG. 3, were obtained. Three of the peptides were common to both preparations indicating identity between the two independent isolations. Four of the tryptic peptides (LILGKPLGEGCFGQVVLA, IADFGLAR, MAPEALFDR and IYTHQSDVWSFGV, See Table I and FIG. 3) were homologous to consensus sequences for tyrosine kinase domains (FIG. 6). This was consistent with the finding that tyrosine kinase activity is associated with the bFGF receptor as described in Huang and Huang, *J. Biol. Chem.* 261:9568 (1986). Thus, the purified protein was determined to be a purified bFGF receptor in that it bound to bFGF, was the expected molecular weight of the receptor, and contained tyrosine kinase sequences.

As discussed above the amino acid sequences of 11 of the 14 peptides were identified in a previously published sequence of a partial human cDNA clone, termed flg (fms-like gene). See M. Ruta et al., *Oncogene*, 3: 9 (1988). That sequence was isolated on the basis of its homology to the proto-oncogene sequence and was not previously recognized to encode a transmembrane receptor protein.

EXAMPLE 2

Isolation of a Full-Length Chicken bFGF Receptor cDNA Clone

A chicken embryo (day 6) cDNA library was constructed from size-selected poly A$^+$mRNA. 200 µg of poly A$^+$mRNA was size-fractionated on a 10%–30% sucrose gradient and fractions containing mRNA greater than or equal to 3.5 Kb were pooled. 5 µg of the sized mRNA was used to generate the cDNA according to the method of U. Gubler and B. Hoffman, *Gene* 25:263 (1983) using a cDNA synthesis kit from Pharmacia (cat.#27-9260-01). The synthesized cDNAs were size-selected for cDNAs greater than or equal to 2.0 kb, and the sized cDNAs were then cloned into the Eco RI site of the bacteriophage vector ZapII (Stratagene, cat.#236211). The resultant cDNA library contained 2.0×10$^6$ independent recombinants.

The library was screened with a $^{32}$P-labeled oligonucleotide probe that encoded the two contiguous peptides shown in FIG. 3 (TVALGSNVEFVCK and VYSDPQPHIQWLK). The oligonucleotides were prepared using a commercial automated oligonucleotide synthesizer. Two 43–45 base oligonucleotides containing a 12 base overlapping complementary sequence were annealed and labeled by Klenow fill-in with dNTP's (-dCTP), $^{32}$P-dCTP, and DNA polymerase Klenow fragment yielding a 70 bp labeled probe. Filters were hybridized under low stringency conditions (20% formamide, 5×standard saline citrate (SSC) and 5×Denhardt's solution at 42° C.) and washed with 0.2×SSC at 42° C. Twenty-five positive clones were isolated following 3 rounds of plaque purification. Of the 25 positive clones, 11 hybridized at high stringency to the human FGF-R cDNA labeled by nick translation and used as a probe (see Example 3). All of the 11 clones were essentially identical except for variation in length at the 5' end of the clones. The amino acid sequence of the largest clone (3.2 kb) contained the sequence of all 14 of the receptor peptides obtained in the protein purification described above (See FIG. 3) and contained the complete coding sequence of the FGF-R. The transmembrane region and the hydrophobic signal sequence were identified by Kyte and Doolittle hydropathy analysis as described in Kyte and Doolittle, *J. Mol. Biol.*, 157:105 (1982).

Figures 5A, 5B:
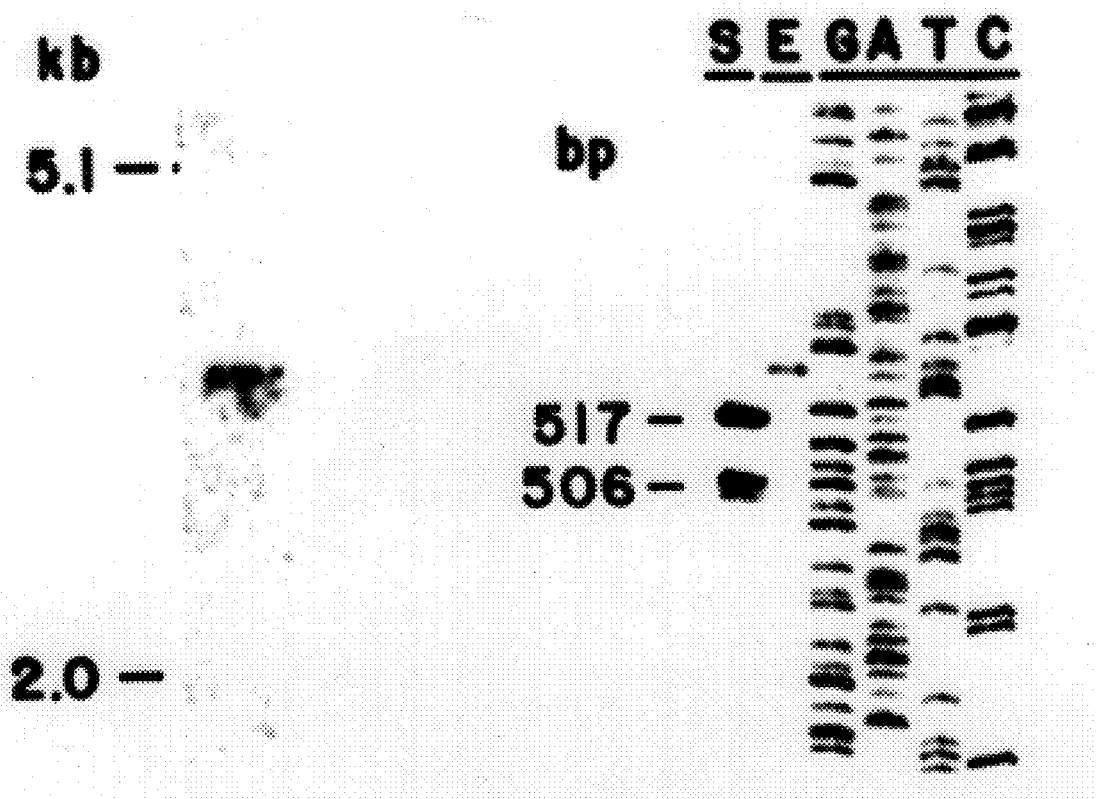
FIG. 5(A) represents an autoradiograph of a northern blot of chicken RNA probed with a full length cDNA chicken bFGF receptor under high stringency conditions.
FIG. 5(B) represents an autoradiograph of a primer extension of chicken mRNA subjected to electrophoresis on an acrylamide sequencing gel.

A single hybridizing band of approximately 3.5 Kb was identified by probing chicken embryo poly(A)$^+$RNA (5 µg) with full-length chicken bFGF receptor cDNA under high stringency conditions (50% formamide, 5×Denhardt's solution and 5×SSC at 42° C. Filters were then washed with 0.2×SSC at 65°. The 3.5 kb single hybridizing band identified by the RNA blot analysis is shown in FIG. 5(A). Primer extension experiments with an oligonucleotide complementary to a sequence near the 5' end of the clone were performed. Chicken embryo poly(A)⁺RNA (5 μg) was denatured with 10 mM methylmercury, annealed to $^{32}$P-labeled primer (5' CTGCACGTCATCGCGCA-3') and extended with murine Moloney leukemia virus reverse transcriptase. (See FIG. 5(B): lane (S) represents $^{32}$P-labeled DNA molecular size standards (1 kb); Lane (E) represents extended fragment (523 nucleotides); Lanes (G, A, T, and C) represent a 5% acrylamide sequencing gel. The data predicted that the mRNA of the receptor was 48 nucleotides longer than the isolated clone.

The amino acid sequence of the longest open reading frame (2.4 kb) included an in-frame stop codon (amino acid residue −12) followed by an initiator methionine (residue 1) and the entire receptor coding sequence (FIG. 3). The cDNA encoded a protein with a deduced molecular mass of 91.7 kD that had features found in several known growth factor receptors. It contained a single-membrane spanning region, an NH$_2$-terminal hydrophobic signal sequence, three extracellular immunoglobulin-like domains and an intracellular tyrosine kinase domain (FIG. 6). Eleven potential N-linked glycosylation sites were also found. N- and O-linked glycosylation of the chicken bFGF receptor may account for the disparity between the observed size of the bFGF receptor and the size predicted from the cDNA sequence.

Three immunoglobulin-like domains in the putative extracellular region were identified on the basis of three criteria: (i) the presence of two characteristic cysteine residues in each domain; (ii) the presence of a consensus tryptophan residue 11 to 12 amino acids on the COOH-terminal side of the first cysteine residue in each immunoglobulin-like domain; and (iii) the presence of the consensus sequence, DXGXYXC, on the NH$_2$-terminal side of the second cysteine residue in each immunoglobulin-like domain. The interleukin-1 (IL-1) receptor also has three immunoglobulin-like domains, and bFGF has 25–30% sequence identity to IL-1. Five immunoglobulin-like domains are present in the receptors for platelet-derived growth factor (PDGF) and colony-stimulating factor-1 (CSF-1).

Between the first and second immunoglobulin-like domains, the bFGF receptor has a feature not found in other members of the immunoglobulin superfamily. There is a series of eight consecutive acidic residues (EDDDDEDD) followed by three serine residues and two additional acidic residues (FIG. 3). Although uninterrupted stretches of 7 to 35 acidic residues have been described for several intracellular proteins, in particular nuclear proteins, such acidic regions are unusual in the extracellular region of transmembrane receptor proteins.

Another unusual feature is the length of the juxtamembrane region, the region between the membrane spanning segment and the kinase domain. This region is normally conserved among receptor tyrosine kinases. For example, the juxtamembrane region is consistently 49 to 51 residues in length in the receptors for PDGF, CSF-1, epidermal growth factor (EGF), human epidermal growth factor-2 (HER2) and insulin. The bFGF receptor has an unusually long juxtamembrane region of about 87 residues.

The cytoplasmic region of the amino acid sequence is about 424 residues long and contains a tyrosine kinase sequence (about residues 482 to 759). Overall, the kinase region of the bFGF receptor shares the most sequence identity (about 51 to 53%) with the PDGF and CSF-1 receptors. The bFGF receptor contains the GXGXXG motif and the conserved lysine residue (about residue 512) that form part of the adenosine 5'-triphosphate (ATP) binding site of tyrosine kinases. The bFGF receptor also contains the two characteristic tyrosine kinase motifs, HRDLAARNVL and DFGLAR, and a tyrosine (about residue 651) at the position analogous to the major phosphorylation site of pp60$^{v-src}$ (about Tyr 416).

The kinase coding sequence of the bFGF receptor, defined by homology to other tyrosine kinases, is split by an insertion of 14 amino acids. The length of the insertion in the kinase region is shorter than that found in the receptors for PDGF and CSF-1 (104 and 70 amino acids, respectively) and is similar to the length of the inserted sequence in the receptors for insulin and insulin-like growth factor-I.

EXAMPLE 3

Full Lenath Human FGF Receptor cDNA Clone Preparation

A human FGF receptor cDNA clone was isolated from a human endothelial cell CDNA library obtained from E. Sadler (R. D. Ye T-C Wun & J. E. Sadler, *J. Biol. Chem.*, 262: 3718–3725 (1987)) using the same oligonucleotide probe described in Example 2.

The endothelial library was hybridized at high stringency with labeled probe 1×10⁶ cpm/ml (50% formamide, 5×SSC, 5×Denhardts, 10 mM NaPO$_4$, pH 6.5, 100 μg/ml salmon sperm DNA at 42° C., (16–24 hrs) and washed at 65° C. with 0.2×SSC, 0.1% SDS.

From the initial screening of the human endothelial cell cDNA library, four clones were identified and purified through 3 rounds of plaque purification. The cDNA inserts from three of these clones generated identical sequences and contained sequences highly homologous to the sequences of tryptic fragments from the purified chicken bFGF-R. The amino acid and nucleic acid sequence of the largest clone (approximately 3.6 kb) is set forth in FIG. 4. Amino acids about 1–21 represent the hydrophobic signal sequence, about 22–285 the extracellular region containing the ligand-binding domain, about 286–306 the transmembrane region and about 307–731 the cytoplasmic region containing tyrosine kinase domain. This method also isolated other highly related human FGF receptors.

EXAMPLE 4

Human aFGF-R cDNA Clone Preparation

Human endothelial cell or placental libraries are screened with full-length FGF-R probes or probes containing a portion of the sequence for FGF-R. Hybridization is performed at low stringency conditions and washed in increments of increasingly higher stringency. The low and high stringency conditions described in Examples 2 and 3 are followed. Between each increment, autoradiography is performed. Clones which are positive through to the most stringent conditions are most related to the bFGF receptors previously described in Examples 2 and 3. Clones which are positive at relaxed stringency but are no longer positive at high stringency conditions are more distantly related. All related but not identical (to FIG. 4) clones are determined by restriction mapping and DNA sequencing. All related clones are selected, subcloned and expressed. The expressed FGF-related cDNAs are then tested for their ability to bind the various FGFS, i.e. acidic FGF.

Alternatively, two probes are designed, one probe containing intracellular FGF-R sequence and the other extracellular FGF-R sequence. Triplicate filters are made. One filter is hybridized at high stringency (see Examples 2 and 3) with the intracellular FGF-R probe. Two filters are hybridized with the extracellular probe, one filter at high stringency and one at low stringency. Since acidic and basic FGFs have only 55% sequence identity, their receptors may also exhibit about 55% sequence identity in the ligand-binding domain. Clones which are positive at high stringency to the intracellular probe and positive only at low stringency to the extracellular probe are FGF-R related receptors. Thus clones are selected, restriction mapping performed, sequenced, and expressed. The expressed receptors are tested for their ability to bind to various FGFs, e.g., acidic FGF.

EXAMPLE 5

Characterization of Human FGF-R cDNA Clones

Plasmid Constructions.

For transfection experiments, full-length chicken FGF receptor cDNA containing 46 nucleotides of 5' nontranslated sequence and the entire 3' nontranslated sequence, and full-length human h2 cDNA containing 13 nucleotides of 5' nontranslated sequence and the entire 3' nontranslated sequence were individually subcloned into the BamHI/SalI sites of the mammalian expression vector pSV7d (P. Luciw, Chiron Corporation). This placed the receptor cDNA fragments in the proper orientation directly downstream from an SV40 promoter element.

To prepare constructs to be used as templates for generating in vitro transcribed RNAs, full-length chicken FGF receptor cDNA was subcloned into the BamHI/SalI sites of Bluescript Sk (Stratagene) and full-length human FGF receptor cDNAs (h2 and h3) were subcloned into the PstI/SalI sites of Bluescript KS. This placed the receptor sequences directly downstream from the T7 RNA polymerase promoter element. To enhance the possibility of efficient translation, ATG sequences upstream of the initiator methionine residue were removed prior to subcloning, leaving 46 and 13 nucleotides of intact 5' nontranslated sequence for the chicken and human constructs, respectively.

Cell Lines and Transfections.

Rat L6 skeletal muscle myoblasts (ATCC CRL 1458) were grown in DME H21 containing 10% fetal calf serum and transferred into opti-MEM (GIBCO) just prior to transfection. Within 24 hours after plating, 1×10$^6$ cells were cotransfected with 20 μg of the appropriate expression construct (either cFGFR/pSV7d or h2FGFR/pSV7d) and 1 μg of a vector containing the neomycin resistance gene (pSV2neo). Cells were transfected using 50 μg of Lipofectin (Bethesda Research Laboratories) following the protocol provided by the manufacturer. Sixteen hours later, an equal volume of DHE H21 media containing 20% fetal calf serum was added. After 48 hours, cells were harvested and passaged (1:10) into selection media (DME H21, 10% fetal calf serum, 500 μg/ml geneticin (GIBCO). Transfectant colonies were assayed for expression of the FGF receptor by immunoblotting with anti-receptor peptide polyclonal antisera.

Affinity Labeling.

Recombinant human aFGF and human bFGF were generously donated by Chiron Corporation and indicated. For affinity labeling experiments, 5×10$^6$ cells were incubated for 30 minutes at 37° C. with 0.1 pmoles of $^{125}$I-aFGF or $^{125}$I-bFGF in the presence or absence of a 200-fold excess of the corresponding unlabeled ligand. The cells were then washed once with ice cold DME H21 containing 20 mM HEPES pH 7.4, 0.2% gelatin, and twice with ice cold PBS. Disuccinimidyl suberate was added to a final concentration of 0.15 mM and incubations were allowed to proceed for 15 minutes at 4° C. The crosslinking agent was then removed and the cells were resuspended in sample buffer containing 100 mM dithiothreitol, boiled for 5 minutes, and subjected to SDS PAGE followed by autoradiography.

In vitro Transcription of RNA.

Prior to transcription, plasmid constructs were linearized with XhoI. RNAs were transcribed from the linearized templates using T7 RNA polymerase in the presence of 500 μM rNTPs (200 μM rGTP) and 500 μM 5' GpppG$^3$, (Pharmacia). Following incubation at 4° C. for 2 hours, transcription reactions were treated with RNAse-free DNAse, phenol extracted, ethanol precipitated, dried and resuspended in water.

Injection of Oocytes.

Animals were anesthetized in a solution of 0.06 percent ethyl p-aminobenzoate. Oocytes were surgically removed and manually dissected into clusters containing 10–20 oocytes. Clusters were incubated in modified Barth Saline (See Maniatis, et al., *Molecular Cloning: A Laboratory Manual*, CSH Press (1982), which is incorporated herein by reference.) MBSH containing 1 mg/ml Type II collagenase (Sigma) for 2 hours at room temperature and then washed extensively with MBSH containing 2 mg/ml bovine serum albumin (BSA). Individual oocytes were maintained at 19° C. in MBSH (1 mg/ml BSA).

Oocytes were injected into the vegetal pole with 50 nl of water or RNA solution (1 μg/μl in water). Following injection, oocytes were incubated at 9° C. for 48 hours before performing $^{45}$Ca$^{++}$efflux assays.

$^{45}$Ca$^{++}$Efflux Assays.

Groups of 50 injected oocytes were added to single wells of a 24 well plate and washed four times with 0.5 ml of a Ca$^{++}$-free MBSH solution containing no BSA. Oocytes were then incubated in 0.5 ml of the wash solution containing $^{45}$CaCl$_2$ (100 μCi/ml) for 3 hours at 19° C. Following incubation, oocytes were washed six times with 0.5 ml of MBSH (1 mg/ml BSA), then transferred to another 24 well plate (5 oocytes per well). All subsequent washes and incubations were performed using 0.5 ml of MBSH containing 1 mg/ml BSA. At 10 minute time intervals, conditioned supernatants were removed from each well and replaced with fresh media. The conditioned media samples were counted individually in a Beckman scintillation counter. When background efflux stabilized, ligands were added to the specified concentrations and media collections were continued.

In 2 out of 16 experiments, oocytes injected with water and stimulated with either aFGF or bFGF exhibited $^{45}$Ca$^{++}$ efflux levels similar to those obtained from oocytes injected with FGF receptor RNA. We have not determined the reason for these unexpected responses, but it is possible that they were due to expression of endogenous FGF receptors on contaminating follicular cells, or on the surface of the oocytes themselves. In all other experiments the water injected oocytes had no significant efflux response whereas the receptor RNA response to FGF was ten to forty fold over the basal measurement.

Receptor levels in injected oocytes have not been measured because our anti-receptor polyclonal antisera nonspecifically recognizes an abundant oocyte protein of approximately the same molecular weight as the FGF receptor on western blots. Furthermore, the levels of exogenous receptors expressed in oocytes appears to be quite low.

Isolation and Characterization of Human cDNA Clones.

Complementary DNA libraries from human placenta and human umbilical vein endothelial cells were generously donated by J. Evan Sadler (Washington University School of Medicine, St. Louis). The libraries were screened with $^{32}$P-labeled oligomers identical to those previously used to identify chicken FGF receptor cDNA clones. Filters were hybridized and washed under high stringency conditions using standard methods. A total of 7 positive clones were isolated after screening 250,000 phage from both libraries. The 4 clones described in this report (h2, h3, h4, and h5) were sequenced by the dideoxy chain termination method, using the Sequenase system (United States Biochemical Corporation). Clones h2, h3, and h4 were obtained from the endothelial cell library and clone h5 was obtained from the placenta library. Nucleotide sequence analyses revealed that all four clones contained identical 5' nontranslated sequences and had poly-A tracts at their 3' ends. However, only the poly-A tract at the 3' end of h2 was preceded upstream by a consensus poly adenylation signal sequence (AATAAA: 37), indicating that internal priming was responsible for the poly A tracts at the 3' ends of the other clones. The h2, h3, h4, and h5 cDNAs contained 0.93 kb, 0.78 kb, 0.95 kb, and 0.2 kb of 3' nontranslated sequence, respectively. The 3' nontranslated sequences of h2 and h3 were identical and the 3' nontranslated sequences of h4 and h5 were also identical. In contrast, the h2/h3' nontranslated sequences were entirely different from the 3' nontranslated sequences of h4/h5.

Polymerase Chain Reactions.

Amplification reactions (42) were carried out using one primer corresponding to the human highly acidic region (approximately amino acids 44–52 in h2; 5'GTTTCTTCTCCTCTGAAGAGGAGT-3') and one degenerate primer corresponding to the IgI domain of the chicken FGF receptor (approximately amino acids 58–69; 5'-GA(TC)GACGTGCAG (A/T)(G/C) CATCAACTGGGTGCGTGATGG-3'). In additional reactions, we used the primer from the human highly acidic region and a second primer derived from the 5' nontranslated region of the human FGF receptor (5'-GAGGATCGAGCTCACTGTGGAGTA-3'). Reaction mixtures contained 750 ng of human genomic DNA, 10 pmoles of each primer, 200 μM of each of the four dNTPs, and 1 unit of Taq polymerase (Perkin Elmer Cetus) in 50 μl of 10 mM Tris-HCl, pH 8.3, 50 mM KCl, 1.5 mM MgCl$_2$, 100 ng/ml BSA. Reactions were carried out in an Ericomp twin block system. Thirty one cycles were performed, consisting of denaturation at 94°C. for 50 seconds, annealing at 65°C. for 1 minute, and extension at 72° C. for 3 minutes.

Isolation and Characterization of Four Unique Human FGF Receptor cDNAs.

The chicken basic FGF receptor contains a single transmembrane domain, an extracellular region containing 3 Ig-like domains and a highly acidic domain, and an intracellular region containing a split tyrosine kinase domain. The chicken FGF receptor cDNA is highly homologous to a previously published partial cDNA (hfla) which encodes a tyrosine kinase that, at the time of its description was of unknown function. The high degree of identity (95 percent) between the chicken bFGF receptor and human flg suggested that hflg was the human counterpart of the bFGF receptor. To obtain full-length human FGF receptor cDNAs, oligonucleotide probe based on the hflg DNA sequence was used to screen a human umbilical vein endothelial cell cDNA library and a human placenta cDNA library. From the initial screenings of 250,000 plaques from each library, four positive clones were isolated from the endothelial cell library and three from the placenta library.

Figure 8:
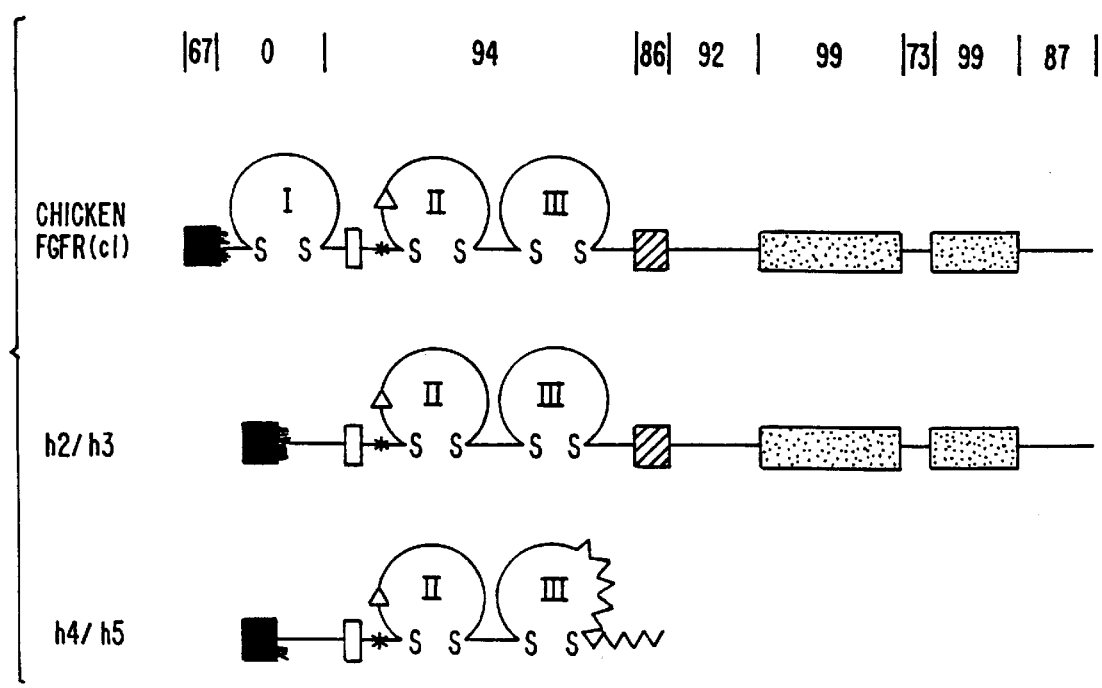
FIG. 8 provides a schematic representation of various different FGF receptors. The following structural features are identified: hydrophobic putative signal sequence (solid boxes), the highly acidic region (open boxes), transmembrane domain striped boxes), kinase 1 and kinase 2 domains (stippled boxes), and the divergent region of h4/h5 (zigzag line). Asterisks indicate the position at which h2 and h4 contain the sequence ArgMet, the chicken receptor contains a single Asn residue, and h3 and h5 contain no corresponding residues. Triangles indicate the position at which h3 contains a Glu residue and all other receptor forms contain a Lys residue. The numbers at the top of the figure indicate the degrees of amino acid identities between similar domains of the h2 human receptor and the chicken receptor.

The CDNA clones could be divided into two classes based on different patterns of restriction maps at their 3' ends. One of these classes derived from cDNA clones which were much shorter in length. Representatives of each class were present in the clones isolated from either library. Two clones (h2 and h3) representing the class of larger cDNA clones, and two clones (h4 and h5) representing the class of shorter cDNA clones were sequenced in their entirety. The deduced amino acid sequences of the four human receptor forms are shown in comparison to the chicken FGF receptor sequence in FIG. 7. A schematic representation of the different receptor forms is shown in FIG. 8.

The predicted amino acid sequences of the h2 and h3 clones are virtually identical and differ only by three amino acids (amino acids 59, 60, and 103 in h2, FIG. 7). At the nucleotide level, h2 and h3 differ only at the positions encoding these three amino acid residues. The h2/h3 open reading frames include a hydrophobic signal sequence and the unusual acidic domain (8 consecutive acidic residues with accompanying residues) that was initially noted in the published sequence of the chicken FGF receptor cDNA. The extracellular domains of h2 and h3 are highly homologous to the chicken FGF receptor except that h2 and h3 lack the sequences of one Ig-like domain (labeled I in FIG. 8). The transmembrane region and cytoplasmic domains are highly homologous to the corresponding domains of the chicken FGF receptor.

The coding sequences of the short cDNA clones, h4 and h5, differ only by two amino acids (positions 59 and 60 in h4; the nucleotide sequences of h4 and h5 differ only at the positions encoding these two residues). The signal sequence, acidic region and one of the Ig-like domains (IgII) are essentially identical to the corresponding regions of h2 and h3. The distinctive feature of h4 and h5 is the Ig-like domain (IgIII) nearest the transmembrane domain. Approximately half of this domain is identical to the corresponding sequence of h2 and h3. However, the carboxyl terminal half of this Ig-like domain is unrelated to h2 and h3 sequences. Unlike h2, h3, and the chicken FGF receptor DNA, h4 and h5 do not encode a hydrophobic membrane spanning region or a cytoplasmic domain.

The sequences of all of the human cDNAs which have been isolated contain only 2 Ig-like domains. To determine whether the human FGF receptor gene contains sequences encoding the first Ig-like domain (IgI), polymerase chain reactions were performed on genomic DNA isolated from human foreskin fibroblasts (HFFs). For these experiments, we utilized one amplifying primer based on the sequence of the IgI domain of the chicken receptor (corresponding to amino acids 58–69), and a second primer based on sequence from the acidic region of the human receptor (amino acids 44–52 in h2). Using these primers, a single 1.3 kb genomic fragment was amplified. As shown in FIG. 9, this fragment contained coding sequences homologous (approximately 83 percent amino acid identity) to the IgI domain of the chicken FGF receptor. In addition, an intron sequence of approximately 1.0 kb separates these coding sequences from sequences encoding the highly acidic region of the receptor. Thus, the human FGF receptor gene clearly contains sequences encoding the IgI domain not found in the human cDNA clones. Furthermore, the presence of an intron between the IgI domain sequence and the acidic region sequence suggests that expression of 2 or 3 Ig domain forms may be regulated by alternative splicing.

To determine whether a 3 Ig domain form of the receptor is expressed in HFF cells, we performed PCR on cDNA generated from HFF mRNA. Using the primers described above, a single 0.24 kb fragment was amplified from HFF DNA. This fragment contained sequences encoding the IgI domain and the acidic region, but no intron sequences. Thus, we conclude that HFF cells transcribe a 3 Ig domain form of the receptor. To determine whether HFF cells also express a 2 Ig domain form of the receptor, we utilized the acidic region primer and a second primer based on sequence from the 5' nontranslated region of the human FGF receptor. In these reactions a 0.23 kb fragment was amplified which, in the same manner as our cDNA clones, was missing sequences corresponding to the IgI domain. Thus, a 2 Ig domain form of the receptor is also transcribed in HFF cells.

Receptors Containing 3 Ig-like and 2 Ig-like Domains Bind Acidic FGF and Basic FGF.

Figure 10:
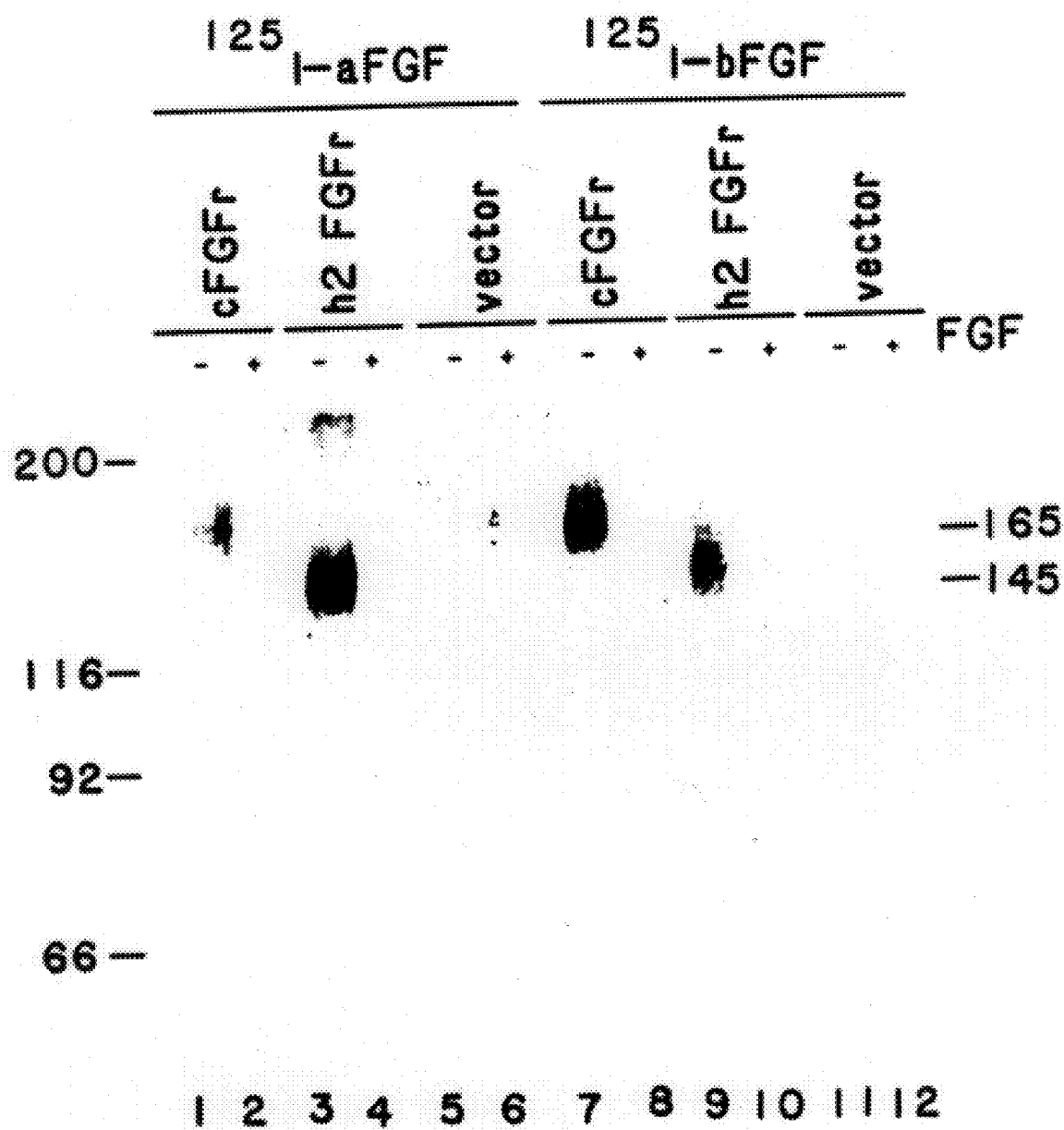
FIG. 10 shows crosslinking of acidic or basic FGF to receptors in cells transfected with FGF receptor cDNAs. L6 cells ($5 \times 10^5$) transfected with the cFGFR/pSV7d expression construct (lanes 1, 2, 7, and 8), the h2FGFR/pSV7d expression construct (lanes 3, 4, 9, and 10), or with vectors alone (lanes 5, 6, 11, and 12) were incubated with 0.1 pmoles of $^{125}$1-aFGF (lanes 1–6) or $^{125}$I-bFGF (lanes, 7–12) in the presence or absence of a 200-fold excess of unlabeled aFGF (lanes 2, 4, and 6) or bFGF (lanes 8, 10, and 12). Binding was performed for 30 minutes at 37° C. Cells were then washed twice with ice cold DME H21 containing 20 mM HEPES pH 7.4, 0.2% gelatin, and twice with ice cold PBS. Disuccinimidyl suberate (DSS) was added to a final concentration of 0.15 mM and crosslinking was allowed to proceed for 15 minutes at 4° C. Samples were resuspended in sample buffer then subjected to SDS PAGE followed by autoradiography.
Figure 11A:
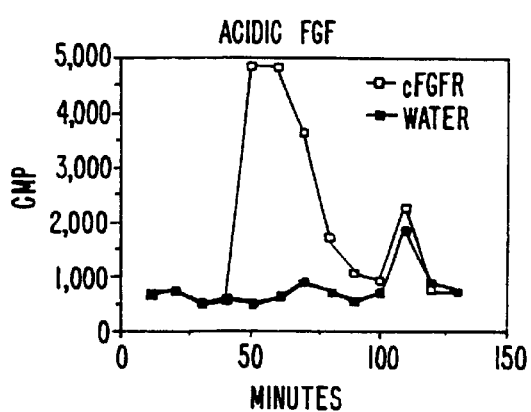
FIG. 11 illustrates acidic and basic FGF induction of a $^{45}Ca^{++}$ efflux from Xenopus oocytes injected with RNA encoding a chicken FGF receptor or the h2 human FGF receptor. The graphs show $^{45}Ca^{++}$ efflux from oocytes injected with chicken FGF receptor RNA (A and C, open squares), human h2 RNA (B and D, open squares), human h3 RNA (B and D, solid triangles) or water (A–D, solid squares). Injected oocytes were incubated with $^{45}CaCl_2$ for 3 hours at 19° C. and then washed extensively. Groups of 5 oocytes were placed in individual wells of a 24 well plate and 0.5 ml of media was added. At 10 minute intervals, the media was removed for counting and fresh media was added. After 40 minutes, aFGF (panel A and B) or bFGF (panel C and D) were added to a final concentration of 0.5 nM. As a positive control, carbachol was added after 100 minutes. Each data point represents the average of triplicate wells.
Figure 11C:
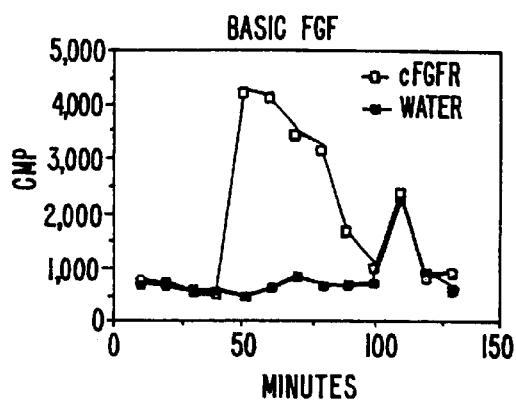
Figure 11B:
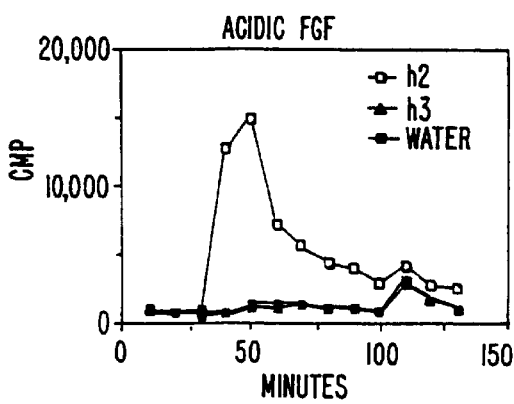
Figure 11D:
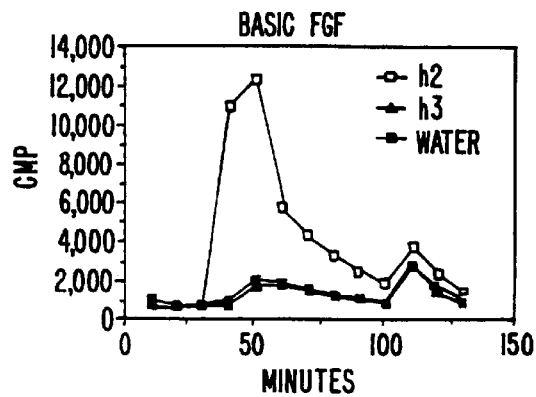

Since the 3 Ig domain receptor (initially isolated from a chicken cDNA library) was purified on the basis of its affinity for basic FGF, it was of interest to determine whether this receptor also binds acidic FGF. To address this question, the 3 Ig domain chicken receptor was expressed in rat L6 myoblasts, a cell line which normally does not express FGF receptors. In addition, the 2 Ig domain human h2 receptor was also expressed in L6 cells. FIG. 10 shows an affinity labeling experiment performed with transfected cells. Cells were incubated with either $^{125}$I-aFGF or $^{125}$I-bFGF and bound ligand was crosslinked in the presence of disuccinimidyl suberate (0.15 mM). Using either ligand, single crosslinked bands were seen in cells transfected with receptor cDNAs (lanes 1, 3, 7, and 9), but not in cells transfected with vector alone (lanes 5, 6, 11, and 12). Subtraction of the molecular weight of FGF (17 kd) from the size of the crosslinked complexes yields estimated molecular weights of 145 kd for the 3 Ig domain form of the receptor and 125 kd for the 2 Ig domain form of the receptor. Excess unlabeled ligands block formation of the crosslinked complexes (lanes 2, 4, 8, and 10). These results demonstrate that both the 3 Ig domain form and the 2 Ig domain form of the FGF receptor are capable of binding either acidic or basic FGF. Scatchard binding analyses indicate that half-maximal binding of $^{125}$I-aFGF to either the 3 Ig domain form or the 2 Ig domain form occurs at a concentration of 0.05 nM. Similarly, half-maximal binding of $^{125}$I-bFGF to either the 3 Ig domain form or the 2 Ig domain form occurs at 0.1 nM.

A Three Ig Domain FGF Receptor and a Two Ig Domain FGF Receptor Mediate Biological Responses to Both Acidic and Basic FGF.

To determine whether any of the membrane spanning forms of the FGF receptor are activated by either aFGF or bFGF, we expressed these receptors in Xenopus oocytes and measured receptor activation using a sensitive $Ca^{++}$ efflux assay. This assay has been used to examine expression of receptors for other $Ca^{++}$ mobilizing ligands including cholecystokinin, bombesin, vasopressin, and angiotensin II. Ligand-induced efflux reflects a mobilization of $Ca^{++}$ from intracellular stores, leading to increased levels of intracellular $Ca^{++}$ and accelerated efflux. For our experiments full-length cDNA were transcribed in vitro and the capped mRNAs were injected into Xenopus oocytes. After 48 hours, the injected oocytes were loaded with $^{45}CaCl_2$ and ligand-dependent calcium mobilization was assayed by measuring $^{45}Ca^{++}$ efflux (FIG. 11). Addition of either aFGF (A and B) or bFGF (C and D) induced a rapid and large efflux of $^{45}Ca^{++}$ from oocytes injected with RNA encoding the chicken FGF receptor (A and C) or RNA encoding the human h2 receptor (B and D). In contrast, oocytes injected with either human h3 RNA (B and D) or water alone (A–D) showed no response to either aFGF or bFGF. As a positive control, carbachol was added following the 100 minute timepoint. Oocytes express endogenous receptors for carbachol, and oocytes injected with either FGF receptor RNA or water exhibited a positive response after carbachol stimulation. We conclude that both the 3 Ig domain form (cFGF-R) and the 2 Ig domain form (h2) of the FGF receptor are biologically responsive to both acidic and basic FGF. Thus, the ligand binding domains for acidic and basic FGF appear to lie in the receptor region encompassing the highly acidic domain and the IgII and IgIII domains.

While the human h2 receptor clearly responds to both ligands, no response was seen in oocytes injected with RNA encoding the h3 receptor form. It is possible that the three amino acid differences between h2 and h3 cause these proteins to respond differently. Alternatively, the lack of a response in oocytes injected with the h3 RNA may be due to unusually low expression levels of the h3 protein. Unfortunately, we have not yet been able to determine receptor protein expression levels in oocytes.

FGF-R forms having either 2 or 3 extracellular Ig-like domains will bind and respond to both acidic and basic FGF. Some forms of FGF receptor mRNA encode only the extracellular domain of the FGF receptor, a protein that is likely to be secreted from the cell.

The fact that a 2 Ig-like domain form of the FGF receptor (h2) binds both aFGF and bFGF with high affinity has allowed us to localize the binding domains for these ligands to a region encompassing the highly acidic region and the IgII and IgIII domains.

The h4 and h5 receptor forms lack transmembrane sequences and presumably represent secreted forms of the FGF receptor. Preliminary data indicates that cells transfected with the h4 cDNA secrete a 70 kd protein which is recognized by anti-FGF-R polyclonal antisera.

The role of secreted forms of the FGF receptor is unclear. The secreted forms may act to regulate levels of extracellular FGFs, and thereby regulate availability of FGFs to cell surface FGF receptors. Alternatively, the secreted FGF receptors may serve to store and sequester FGFs at a particular location. Another possibility is that the secreted forms may bind to FGFs in an intracellular compartment and subsequently serve as a means for secreting the factor. This is an important consideration in view of the fact that aFGF and bFGF do not contain signal sequences and their mechanism of secretion is unknown.

our results suggest that receptor diversity can be generated by alternative splicing. We have isolated a total of 5 different FGF receptor cDNA species. Comparison of amino acid sequences strongly indicates that all 5 species are derived from the same gene. Another interesting feature of the human receptor forms is the presence or absence of the ArgMet sequence (amino acids 59 and 60 in h2 and h4) in the extracellular domain.

Affinity labeling experiments using either $^{125}$I-aFGF or $^{125}$I-bFGF identified a single 145 kd receptor protein on transfectant cells expressing the 3 Ig domain form of the FGF receptor, and a single 125 kd receptor protein on transfectant cells expressing the 2 domain form of the FGF receptor (see FIG. 11). It is possible that the presence of two receptor species may reflect coexpression of the 3 Ig domain and 2 Ig domain forms of the receptor. Our data clearly establish that a single FGF receptor species can bind both aFGF and bFGF with high affinity and mediate the biological effects of these factors. We have used acidic and basic FGF in these experiments because they are the best characterized members of the FGF family, and are readily available in recombinant form.

EXAMPLE 6

Competitive Binding of FGF-R Peptides or Fragments Development of FGF-R Related Antagonists or Agonists A fragment containing all or part of the extracellular, ligand-binding domain of the FGF-R (i.e., containing amino acids 22–374 of FIG. 3 or 22–285 of FIG. 4) or analogs thereof are expressed in a host (e.g. mammalian cells or baculovirus infected insect cells) and purified as described in Example 1. Alternatively, fragments of the ligand-binding domain are made using a peptide synthesizer (Applied Biosystems) and purified by HPLC. Different concentrations of the FGF-R fragment or analogs thereof (FGF-Rexs) are tested for their ability to block the binding of $^{125}$I-FGF to Swiss 3T3 cells. Competitive binding is performed as described in FIG. 1A in Example 1 using FGF-Rexs instead of unlabeled ligand and competitive binding is determined.

FGF-Rexs are also tested for their ability to inhibit FGF-induced mitogenesis as measured by $^3$H-thymidine incorporation into cells and by counting cell numbers. FGF-Rexs which block binding of FGF to the cell-surface receptor may act as an antagonist and block $^3$H-thymidine uptake and the increase in cell number induced by FGF. FGF-Rexs may also act as agonists, i.e. by dimerization with the cell surface receptor which may mimic a ligand-mediated receptor-recaptor interaction. In such an instance, FGF-Rexs may stimulate mitogenesis in the absence of ligand or may enhance the FGF mediated mitogenic response.

FGF-Rexs are also tested for their ability to inhibit or activate FGF-induced tyrosine phosphorylation of the 90 substrate protein in Swiss 3T3 cells or autophosphorylation of the cell-associated FGF-R. FGF-Rexs which block FGF-induced tyrosine phosphorylation are antagonists. FGF-Rexs which activate autophosphorylation of the cell-associated FGF-R in the absence of FGF are agonists.

FGF-Rexs are also tested for their anti-angiogenic activity. FGF-Rexs are tested first for their ability to inhibit the FGF-induced growth and the mobilization of endothelial cells into vessels in vitro. Angiogenesis is assayed in vitro using an aortic ring assay. Aortic rings are placed in a collagen matrix formed in the presence or absence of FGF and FGF-Rexs. Endothelial cells sprout and form vessels from the aortic ring within a few days in the presence of FGF. The addition of FGF-Rexs which are antagonists in the previous assays inhibit the FGF-induced growth of capillary sprouts. FGF-Rexs which are angiogenic even in the absence of FGF are agonists.

FGF analogs, angiogenic factors, anti-angiogenic factors as well as antibodies to the extracellular portion of the FGF-R are tested for their ability to bind directly or compete for binding of native FGF for binding to purified or expressed FGF-R. In addition, they are tested for their ability to stimulate mitogenesis (agonists) or inhibit FGF-dependent mitogenesis (antagonists) as well as tyrosine phosphorylation in cells expressing the FGF-R. These studies are important in determining if the mode of action of each angiogenic and anti-angiogenic factor, etc., is receptor-mediated and in determining if there is receptor specificity (i.e. acidic versus basic FGF-R) for angiogenic and anti-angiogenic factors.

FGF analogs are radiolabeled and binding is performed with labeled ligand, purified or expressed receptor in the appropriate physiologic buffer (i.e. culture media or phosphate buffered saline (PBS)) for 0.5 at 37° C. or 2–24 hrs at 4° C. The complex is precipitated (5–10% polyethylene glycol, 1 mg/ml IgG) and separated by filtration through filters (i.e. Whitman GFA) and the associated radioactivity determined.

While the invention has been described in connection with certain specific embodiments thereof, it should be recognized that various modifications as may be apparent to one of skill in the art to which the invention pertains also fall within the scope of the invention as defined by the appended claims.

What is claimed is:

1. An isolated nucleic acid encoding a segment of at least seven contiguous amino acids of a human fibroblast growth factor receptor shown in FIGS. 7A and 7B, which segment lacks a tyrosine kinase domain, wherein the segment can specifically bind to an antibody to the human fibroblast growth factor receptor.

2. An isolated nucleic acid of claim 1, wherein said contiguous amino acids are from an IgII domain of a human fibroblast growth factor receptor described in FIG. 7.

3. An isolated nucleic acid of claim 1, encoding a full-length IgII domain of a fibroblast growth factor receptor shown in FIGS. 7A and 7B.

4. An isolated nucleic acid of claim 3, further encoding at least one additional peptide segment from a fibroblast growth factor receptor shown in FIGS. 7A and 7B selected from the group consisting of a signal peptide, an IgI domain, an acidic segment, an IgIII segment, an IgIIIT segment, and a transmembrane segment.

5. An isolated nucleic acid of claim 3, further comprising a transcription promoter sequence.

6. The isolated nucleic acid of claim 1, which encodes at least 13 contiguous amino acids from a fibroblast growth factor receptor shown in FIGS. 7A and 7B.

7. The isolated nucleic acid of claim 6, which encodes at least 20 contiguous amino acids from a fibroblast growth factor shown in FIGS. 7A and 7B.

8. The isolated nucleic acid of claim 1, wherein the segment comprises at least seven contiguous amino acids from the human fibroblast growth factor receptor h3 of FIG. 7A and 7B.

9. An isolated nucleic acid that hybridizes under stringent conditions including 50% formamide, 5×SSC, 5×Denhardt's solution, 10 mM sodium phosphate, pH 6.5, 100 µg/ml salmon sperm DNA and at 42° C. to a segment of a nucleic acid, which segment encodes an IgII domain of a soluble fibroblast growth factor receptor shown in FIGS. 7A and 7B, the isolated nucleic acid lacking a segment encoding a tyrosine kinase domain and wherein the IgII domain can specifically bind to an antibody to the soluble fibroblast growth factor receptor.

10. An isolated nucleic acid of claim 9, wherein said soluble growth factor receptor is h4 or h5.

11. A nucleic acid according to claim 1, 3, or 9, attached to a reporter molecule.

12. An isolated nucleic acid encoding the human fibroblast growth factor receptor designated h3 in FIGS. 7A and 7B.

13. An isolated nucleic acid encoding the human fibroblast growth factor receptor designated h2 in FIGS. 7A and 7B.

14. An isolated cell line transformed with a DNA sequence capable of expressing a polypeptide comprising at least seven contiguous amino acids of an extracellular domain of a fibroblast growth factor receptor shown in FIGS. 7A and 7B, the polypeptide lacking a tyrosine kinase domain and wherein the polypeptide can specifically bind to an antibody to the human fibroblast growth factor receptor.

15. The isolated cell line of claim 14, wherein the polypeptide comprises a soluble form of a human fibroblast growth factor receptor.

16. An isolated cell line as in claim 15, wherein the cell is capable of secreting the human fibroblast growth factor receptor.

17. The isolated cell line of claim 14, wherein the polypeptide comprises at least 13 contiguous amino acids of a fibroblast growth factor receptor shown in FIGS. 7A and 7B.

18. The isolated cell line of claim 14, wherein the polypeptide comprises at least 20 contiguous amino acids of a fibroblast growth factor receptor shown in FIGS. 7A and 7B.

19. The isolated cell line of claim 14, wherein the polypeptide comprises at least seven contiguous amino acids of an extracellular domain of the fibroblast growth factor receptor h3 shown in FIGS. 7A and 7B.

20. A method of making a protein comprising a fibroblast growth factor receptor segment, said method comprising expressing an isolated nucleic acid encoding a segment of at least seven contiguous amino acids of a fibroblast growth factor receptor shown in FIGS. 7A and 7B, which segment lacks a tyrosine kinase domain and wherein the segment can specifically bind to an antibody to the human fibroblast growth factor receptor, and recovering the segment.

21. The method of claim 20, wherein the isolated nucleic acid encodes at least 13 contiguous amino acids from a fibroblast growth factor receptor shown in FIGS. 7A and 7B.

22. The method of claim 21, wherein the isolated nucleic acid encodes at least 20 contiguous amino acids from a fibroblast growth factor receptor shown in FIGS. 7A and 7B.

23. The method of claim 20, wherein the segment comprises at least 7 contiguous amino acids from the fibroblast growth factor receptor h3 of FIGS. 7A and 7B.

24. A method of making a fibroblast growth factor receptor or peptide thereof, the method comprising expressing a nucleic acid in a host cell to produce the fibroblast growth factor receptor or peptide and recovering the fibroblast growth factor receptor or peptide from the host cell or media containing the host cell, wherein the nucleic acid comprises at least 21 bases of a sequence selected from the group consisting of:

a DNA sequence in FIG. 3, a DNA sequence in FIGS. 4A, B, C and D, a DNA sequence in FIG. 9, and a DNA sequence encoding at least seven contiguous amino acids of a polypeptide of FIGS. 7A and B; wherein the fibroblast growth factor receptor or peptide comprises an extracellular domain and lacks a tyrosine kinase domain and wherein the receptor or peptide can specifically bind to an antibody to the human fibroblast growth factor receptor.

25. A method of making a protein comprising a fibroblast growth factor receptor segment, said method comprising expressing an isolated nucleic acid encoding a full-length IgII domain of a fibroblast growth factor receptor shown in FIGS. 7A and 7B to produce the fibroblast growth factor receptor segment and wherein the full-length IgII domain can specifically bind to an antibody to the human fibroblast growth factor receptor, and recovering the fibroblast growth factor receptor segment.

26. A method of forming a composition comprising a fibroblast growth factor segment, comprising:

expressing an isolated nucleic acid encoding a segment of at least seven contiguous amino acids of a fibroblast growth factor receptor shown in FIGS. 7A and 7B, which segment lacks a tyrosine kinase domain, and wherein the segment can specifically bind to an antibody to the human fibroblast growth factor receptor and recovering the segment; and combining the segment with a carrier as a composition.

\* \* \* \* \*